US012570690B2

(12) United States Patent
Knick et al.

(10) Patent No.: US 12,570,690 B2
(45) Date of Patent: Mar. 10, 2026

(54) IMMUNOGLOBULIN BINDING PROTEINS FOR AFFINITY PURIFICATION

(71) Applicant: Navigo Proteins GmbH, Halle/Saale (DE)

(72) Inventors: Paul Knick, Halle/Saale (DE); Hanna Bobolowski, Halle/Saale (DE); Mathias Kahl, Halle/Saale (DE); Erik Fiedler, Halle/Saale (DE); Ulrich Haupts, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 397 days.

(21) Appl. No.: 18/016,440

(22) PCT Filed: Jul. 14, 2021

(86) PCT No.: PCT/EP2021/069564
§ 371 (c)(1),
(2) Date: Jan. 16, 2023

(87) PCT Pub. No.: WO2022/013272
PCT Pub. Date: Jan. 20, 2022

(65) Prior Publication Data
US 2023/0295223 A1 Sep. 21, 2023

(30) Foreign Application Priority Data

Jul. 15, 2020 (EP) ..................................... 20186024
Feb. 23, 2021 (EP) ..................................... 21158714

(51) Int. Cl.
| | |
|---|---|
| *C07K 1/22* | (2006.01) |
| *A61K 39/395* | (2006.01) |
| *C07K 14/00* | (2006.01) |
| *C07K 14/31* | (2006.01) |
| *C07K 16/42* | (2006.01) |

(52) U.S. Cl.
CPC .............. *C07K 1/22* (2013.01); *C07K 14/001* (2013.01)

(58) Field of Classification Search
None
See application file for complete search history.

(56) References Cited

U.S. PATENT DOCUMENTS

| | | | |
|---|---|---|---|
| 11,230,576 B2 * | 1/2022 | Knick | .................... C07K 14/31 |
| 2010/0221844 A1 | 9/2010 | Bian et al. | |
| 2019/0177376 A1 | 6/2019 | Knick et al. | |

FOREIGN PATENT DOCUMENTS

| | | |
|---|---|---|
| EP | 3 650 465 A1 | 5/2020 |
| WO | WO 2017/00942 | 1/2017 |
| WO | WO 2019/152318 | 8/2018 |
| WO | WO 2019/093439 A1 | 5/2019 |
| WO | WO 2011/122943 A1 | 6/2021 |

OTHER PUBLICATIONS

Huse et al. (2002) Purification of antibodies by affinity chromatography. J Biochem Biophys Methods 51:217-231.
International Search Report corresponding to PCT International Patent Application No. PCT/EP2021/069564 dated Oct. 8, 2021.
Written Opinion corresponding to PCT International Patent Application No. PCT/EP2021/089564 dated Oct. 8, 2021.

* cited by examiner

*Primary Examiner* — Manjunath N Rao
*Assistant Examiner* — Jae W Lee
(74) *Attorney, Agent, or Firm* — Jenkins, Taylor & Hunt, P.A.

(57) ABSTRACT

The present invention relates to immunoglobulin (Ig) binding proteins comprising one or more domains having highly hydrophobic amino acids with branched side chains (Iso, Leu, Val), or aromatic amino acids (Tyr, Phe, or Trp) corresponding to position 4 or 6 or 8 of the Ig binding protein of SEQ ID NO: 1 or functionally similar proteins. The novel proteins have superior properties for highly efficient purification methods for antibodies (immunoglobulins), for example, the proteins have high binding capacity and high chemical stability. The invention further relates to affinity matrices comprising the Ig binding proteins of the invention. The invention also relates to a use of these Ig binding proteins or affinity matrices for affinity purification of immunoglobulins and to methods of affinity purification using the Ig binding proteins of the invention.

13 Claims, 3 Drawing Sheets

Specification includes a Sequence Listing.

FIGURE 1. Selected novel Ig Binding proteins.

| SEQ ID | remarks | Sequence (positions 1–58) |
|---|---|---|
| 4 | cs26 8I | IAAQHDKIQQAAFYEILHLPNLTEEQRNAFIQSLRDDPSVSLEILAEAKKLNDAQAPK |
| 6 | cs26 8F | IAAQHDKFQQAAFYEILHLPNLTEEQRNAFIQSLRDDPSVSLEILAEAKKLNDAQAPK |
| 7 | cs26 8Y | IAAQHDKYQQAAFYEILHLPNLTEEQRNAFIQSLRDDPSVSLEILAEAKKLNDAQAPK |
| 8 | cs26 8W | IAAQHDKWQQAAFYEILHLPNLTEEQRNAFIQSLRDDPSVSLEILAEAKKLNDAQAPK |
| 9 | cs26 8L | IAAQHDKLQQAAFYEILHLPNLTEEQRNAFIQSLRDDPSVSLEILAEAKKLNDAQAPK |
| 10 | cs26 6I | IAAQHIKDQQAAFYEILHLPNLTEEQRNAFIQSLRDDPSVSLEILAEAKKLNDAQAPK |
| 11 | cs26 6Y | IAAQHYKDQQAAFYEILHLPNLTEEQRNAFIQSLRDDPSVSLEILAEAKKLNDAQAPK |
| 12 | cs26 6W | IAAQHWKDQQAAFYEILHLPNLTEEQRNAFIQSLRDDPSVSLEILAEAKKLNDAQAPK |
| 14 | cs26 6L | IAAQHLKDQQAAFYEILHLPNLTEEQRNAFIQSLRDDPSVSCEILAEAKKLNDAQAPK |
| 15 | cs26 4I | IAAIHDKDQQAAFYEILHLPNLTEEQRNAFIQSLRDDPSVSLEILAEAKKLNDAQAPK |
| 16 | cs26 4F | IAAFHDKDQQAAFYEILHLPNLTEEQRNAFIQSLRDDPSVSLEILAEAKKLNDAQAPK |
| 17 | cs26 4W | IAAWHDKDQQAAFYEILHLPNLTEEQRNAFIQSLRDDPSVSLEILAEAKKLNDAQAPK |
| 18 | cs26 4L | IAALHDKDQQAAFYEILHLPNLTEEQRNAFIQSLRDDPSVSLEILAEAKKLNDAQAPK |
| 20 | cs26 8I 14H | IAAQHDKIQQAAFHEILHLPNLTEEQRNAFIQSLRDDPSVSLEILAEAKKLNDAQAPK |
| 25 | cs27 8I | IAAKFDEIQQAAFYEILHLPNLTEEQRNAFIQSLRDDPSVSLEVLGEAQKLNDSQAPK |
| 26 | cs27 8I 14H | IAAKFDEIQQAAFHEILHLPNLTEEQRNAFIQSLRDDPSVSLEVLGEAQKLNDSQAPK |
| 27 | cs27 8I 28H | IAAKFDEIQQAAFYEILHLPNLTEEQRHAFIQSLRDDPSVSLEVLGEAQKLNDSQAPK |
| 28 | cs59 8I | IDAKFDEIQQAAFYEILHLPNLTEDQRNAFIQSLRDDPSVSLALLAEAKKLNDAQAPP |
| 29 | cs59 8I 14H | IDAKFDEIQQAAFHEILHLPNLTEDQRNAFIQSLRDDPSVSLALLAEAKKLNDAQAPP |
| 30 | cs59 8I 28H | IDAKFDEIQQAAFYEILHLPNLTEDQRHAFIQSLRDDPSVSLALLAEAKKLNDAQAPP |
| 31 | cs60 8I | IDAKFDEIAQAAFYEILHLPNLTEDQRNAFIQSLRDDPSVSLALLAEAKKLNDAQAPP |
| 32 | cs60 8I 14H | IDAKFDEIAQAAFHEILHLPNLTEDQRNAFIQSLRDDPSVSLALLAEAKKLNDAQAPP |
| 33 | cs60 8I 28H | IDAKFDEIAQAAFYEILHLPNLTEDQRHAFIQSLRDDPSVSLALLAEAKKLNDAQAPP |
| 34 | cs14 8I | IAAKHDKIQQAAFYEILHLPNLTEDQRNAFIQSLRDDPSVSLEILGEAKKLNDAQAPP |
| 35 | cs14 8I 14H | IAAKHDKIQQAAFHEILHLPNLTEDQRNAFIQSLRDDPSVSLEILGEAKKLNDAQAPP |
| 36 | cs14 8I 28H | IAAKHDKIQQAAFYEILHLPNLTEDQRHAFIQSLRDDPSVSLEILGEAKKLNDAQAPP |

FIGURE 2. Remaining activity after NaOH incubation (pos. 8 modifications)
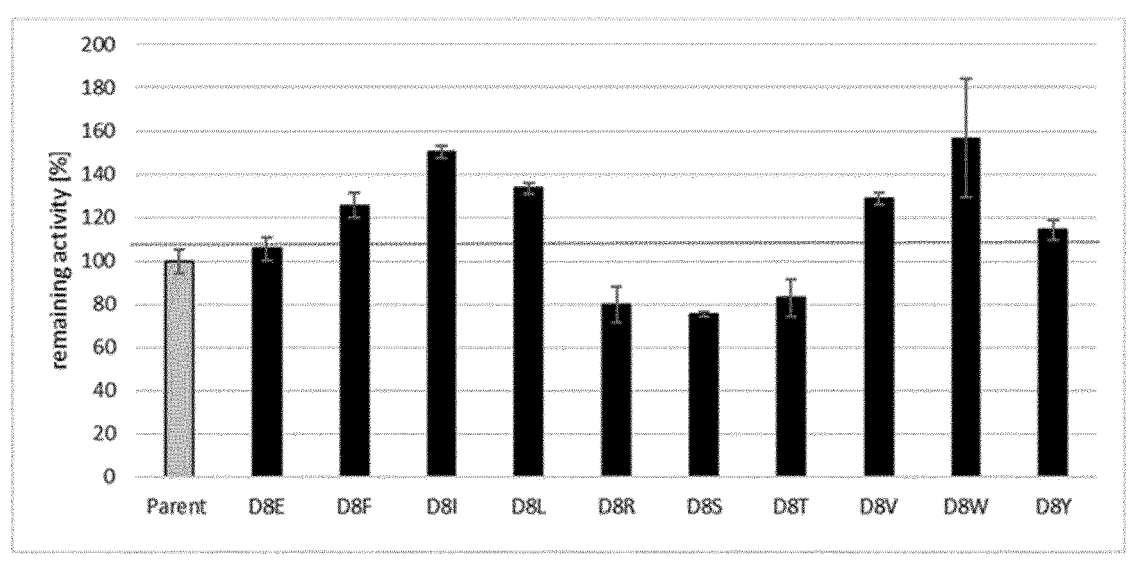
FIGURE 3. Remaining activity after NaOH incubation (pos. 4 modifications)
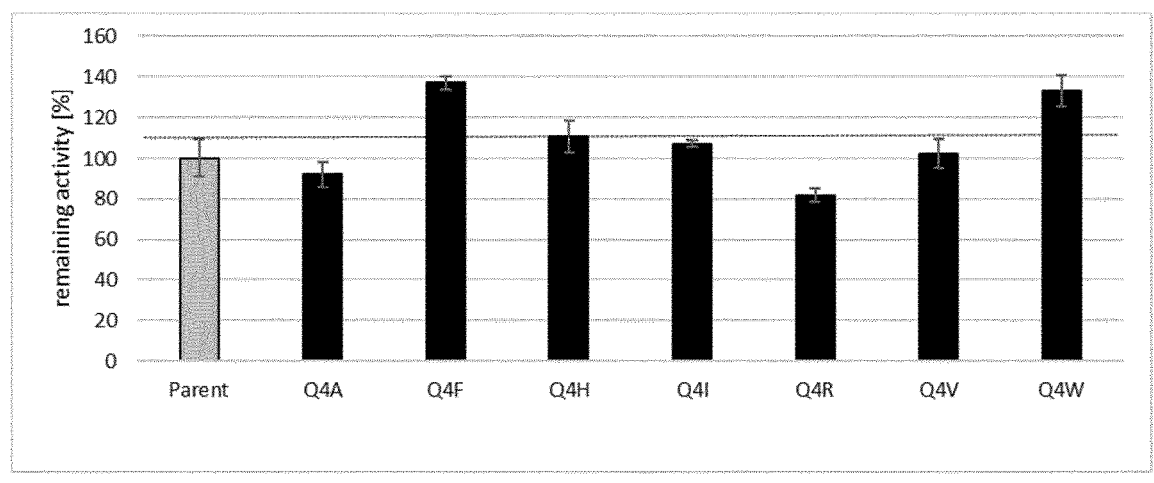
FIGURE 4. Remaining activity after NaOH incubation (pos. 6 modifications)
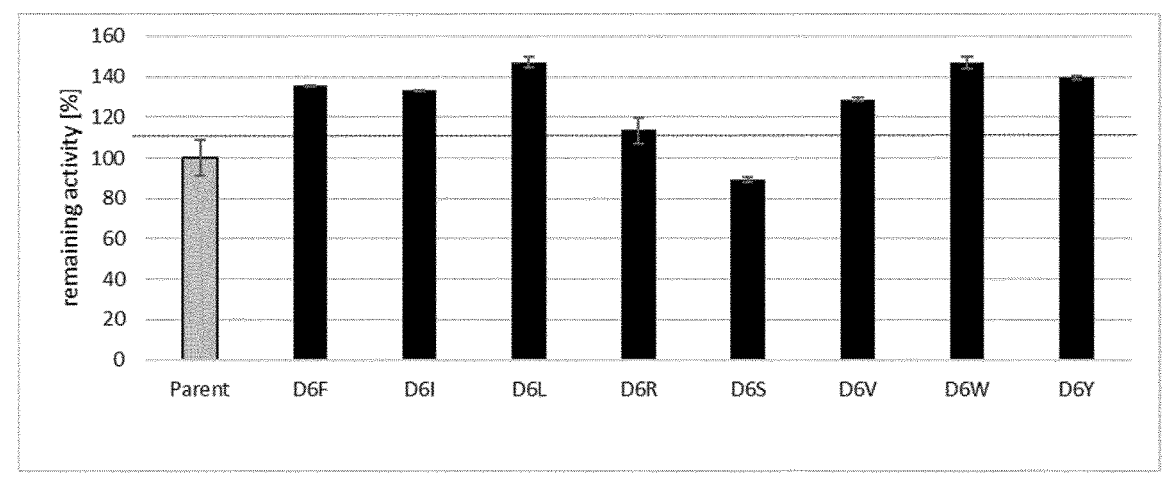

FIGURE 5. Elution profile of Belimumab from affinity ligand SEQ ID NO: 51 (pH gradient pH 6.0 to 2.0)
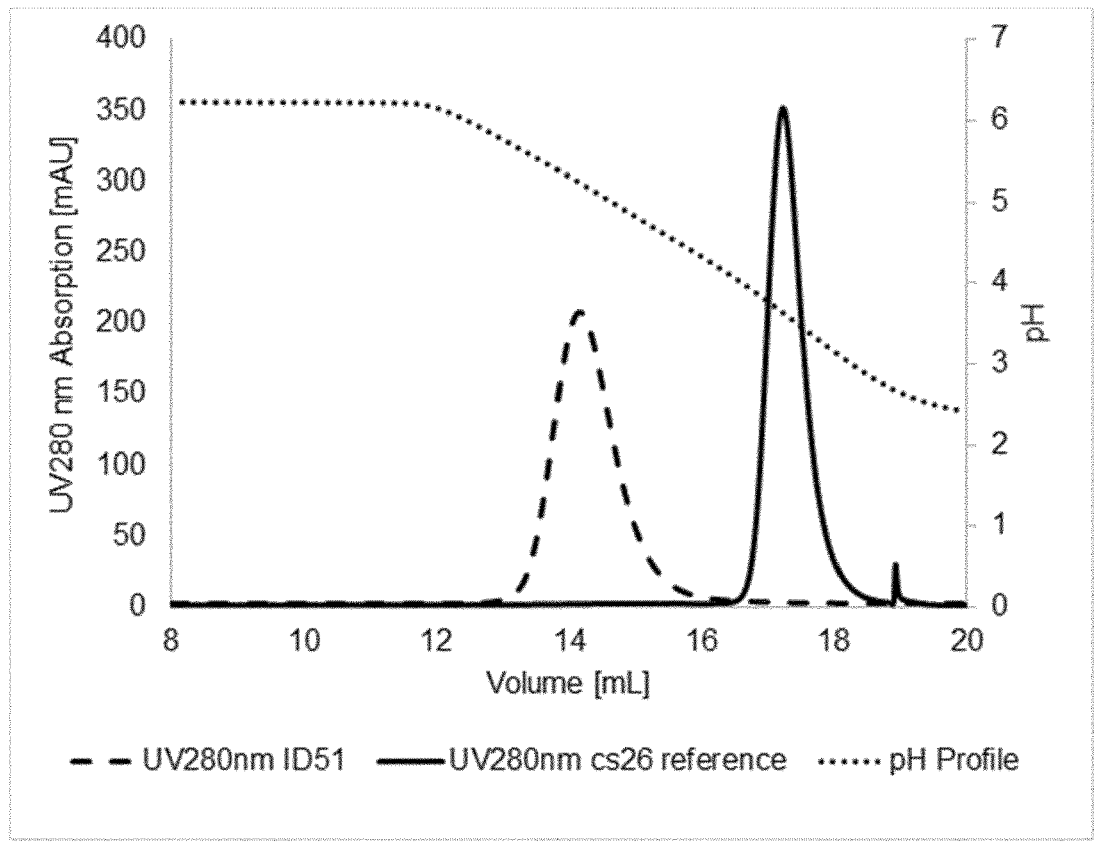
Figure 6. DBC10% determination of affinity ligand SEQ ID NO: 51; the antibody eluted completely at pH 4.8.
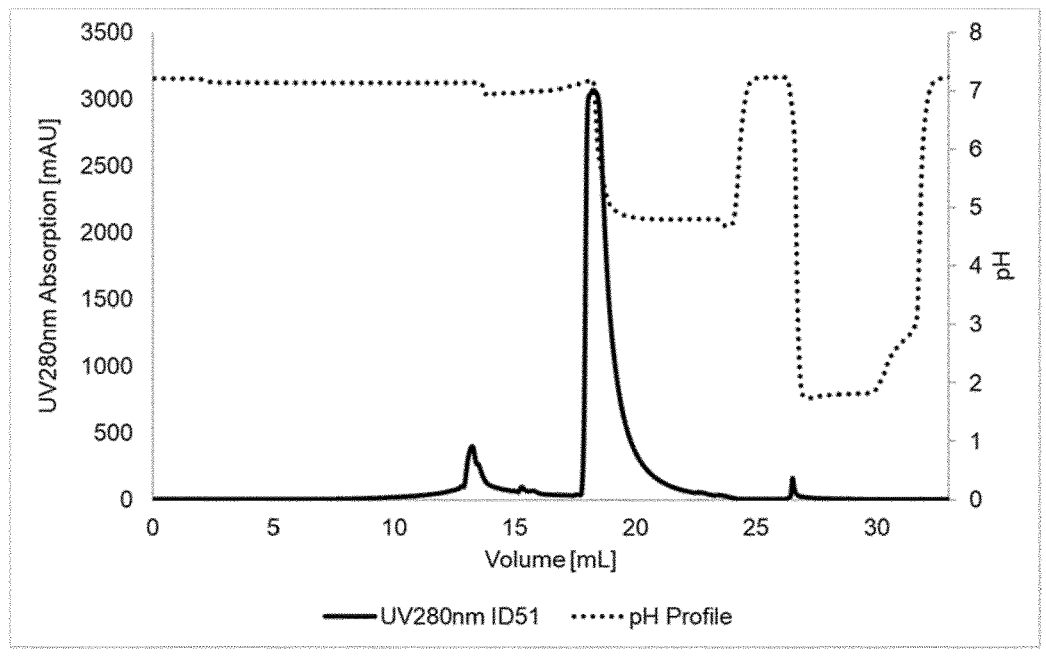

IMMUNOGLOBULIN BINDING PROTEINS FOR AFFINITY PURIFICATION

CROSS REFERENCE TO RELATED APPLICATIONS

The present application is a United States National Stage Application of PCT International Patent Application Serial No. PCT/EP2021/069564, filed Jul. 14, 2021 which itself claims the benefit of European Patent Applications EP 20186024.4, filed Jul. 15, 2020 and EP 21158714.2, filed Feb. 23, 2021. The disclosure of each of these application is incorporated herein by reference in its entirety.

FIELD OF THE INVENTION

The present invention relates to immunoglobulin (Ig) binding proteins comprising one or more domains having highly hydrophobic amino acids with branched side chains (Iso, Leu, Val), or aromatic amino acids (Tyr, Phe, or Trp), corresponding to positions 4 or 6 or 8 of the Ig binding protein of SEQ ID NO: 1 or functionally similar proteins. The novel proteins have superior properties for highly efficient purification methods for antibodies (immunoglobulins), for example, the proteins have high binding capacity and high chemical stability. The invention further relates to affinity matrices comprising the Ig binding proteins of the invention. The invention also relates to a use of these Ig binding proteins or affinity matrices for affinity purification of immunoglobulins and to methods of affinity purification using the Ig binding proteins of the invention.

SEQUENCE LISTING

A Sequence Listing is provided herewith as a Sequence Listing, "3073_26_PCT_US" created on Dec. 15, 2022, and having a size of 39.3 KB. The contents of the Sequence Listing are incorporated by reference herein in their entirety.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface Protein A from *Staphylococcus aureus* as selective ligand for immunoglobulins (see, for example, review by Huse et al., J. Biochem. Biophys. Methods 51, 2002: 217-231). Wild-type Protein A binds to the Fc region of IgG molecules with high affinity and selectivity. Variants of Protein A with improved properties such as alkaline stability are available for purifying antibodies and various chromatographic matrices comprising Protein A ligands are commercially available. However, currently available Protein A based chromatography matrices show a loss of binding capacity for immunoglobulins following exposure to alkaline conditions and require elution conditions at pH below 4.

TECHNICAL PROBLEMS UNDERLYING THE INVENTION

Most large scale production processes for antibodies or Fc-containing fusion proteins use Protein A for affinity purification. However, due to limitations of Protein A applications in affinity chromatography there is a need in the art to provide novel Ig binding proteins with improved properties that specifically bind to immunoglobulins in order to facilitate affinity purification of immunoglobulins. To maximally exploit the value of the chromatographic matrices comprising Ig binding proteins it is desirable to use the affinity ligand matrices multiple times. Between chromatography cycles a thorough cleaning procedure is required for sanitization and removal of residual contaminants on the matrix. In this procedure, it is general practice to apply alkaline solutions with high concentrations of NaOH to the affinity ligand matrices. Wild-type Protein A domains cannot withstand such harsh alkaline conditions for an extended time and quickly lose binding capacity for immunoglobulin. Further, for a repeated use of affinity ligand matrices, a cleaning step under harsh acidic conditions is required.

Accordingly, there is an ongoing need in this field to obtain novel proteins capable of binding proteins comprising an Ig sequence, for example antibodies, and to withstand the harsh cleaning conditions applied in affinity purification of immunoglobulins.

The present invention provides Ig binding proteins that are particularly well-suited for affinity purification of immunoglobulins. In particular, the Ig binding proteins of the invention have several advantages. One significant advantage of the Ig binding proteins of the invention is their improved stability at high pH for a prolonged time period (such as more than 2 days) without reducing the Ig binding capacities in combination with high dynamic binding capacities.

Further, the novel proteins of the invention are particularly useful for affinity purification of antibodies where mild acidic elution conditions are required.

The above overview does not necessarily describe all problems solved by the present invention.

SUMMARY OF THE INVENTION

An aspect of the present invention is to provide an Ig binding protein suitable for affinity purification.

[1] This is achieved with an Immunoglobulin (Ig) binding protein comprising one or more Ig binding domains, wherein at least one Ig binding domain corresponds to an Ig binding protein having at least 80% amino acid identity to SEQ ID NO: 1 (cs26), wherein the amino acid corresponding to positions 4, 6, or 8 of SEQ ID NO: 1 is isoleucine (I) or leucine (L) or an aromatic amino acid. The Ig binding protein is alkaline stable (at least 20 h at 0.5 M NaOH). In various embodiments, an Ig binding protein is comprising one or more Ig binding domains, wherein at least one Ig binding domain corresponds to an Ig binding protein having at least 80% amino acid identity to SEQ ID NO: 1, wherein the amino acid corresponding to position 8 of SEQ ID NO: 1 is isoleucine (I), leucine (L), valine (V) or an aromatic amino acid, and wherein the Ig binding protein is stable under alkaline conditions of 0.5 M NaOH for at least 20 h.

[2] The Ig binding protein according to item [1], wherein
(a) the amino acid corresponding to position 8 of SEQ ID NO: 1 is isoleucine (I) or tyrosine (Y), preferably wherein the amino acid corresponding to position 8 of SEQ ID NO: 1 is isoleucine (I), or (b) wherein the amino acid corresponding to position 4 of SEQ ID NO: 1 is tryptophan (W) or phenylalanine (F), or
(c) wherein the amino acid corresponding to position 6 of SEQ ID NO: 1 is isoleucine (I), tryptophan (W), or tyrosine (Y), or leucine (L).

[3] The Ig binding protein according to item [1] or [2], wherein one or more amino acid(s) corresponding to position 10, 14, 16, 17, 18, or 28 of SEQ ID NO: 1 is/are selected from the group of histidine (H) or acidic amino acids selected from aspartate (D) or glutamate (E), preferably in position 14 or 28. In various embodiments, the Ig binding protein is having at least 80% amino acid identity to SEQ ID NO: 1 (cs26), wherein the amino acid corresponding to position 8 of SEQ ID NO: 1 is isoleucine (I) or leucine (L) or valine (V) or an aromatic amino acid, and the amino acid corresponding to position 14 of SEQ ID NO: 1 is histidine. In various embodiments, the Ig binding protein is having at least 80% amino acid identity to SEQ ID NO: 1 (cs26), wherein the amino acid corresponding to position 8 of SEQ ID NO: 1 is isoleucine (I) or leucine (L) or valine (V) or an aromatic amino acid, the amino acid corresponding to position 14 of SEQ ID NO: 1 is histidine (H), and the amino acid corresponding to position 29 of SEQ ID NO: 1 is lysine (K). Preferably, the amino acid corresponding to position 8 of SEQ ID NO: 1 is isoleucine (I) or leucine (L) or an aromatic amino acid, which may be any of tryptophan (W), phenylalanine (F), or tyrosine (Y). More preferably, the amino acid corresponding to position 8 of SEQ ID NO: 1 is isoleucine (I) or leucine (L), even more preferably the amino acid corresponding to position 8 of SEQ ID NO: 1 is isoleucine (I). In various embodiments, the Ig binding protein may have a cysteine (C) residue at the position corresponding to position 43 or 46 of SEQ ID NO: 1.

[4] The Ig binding protein according to any one of items [1]-[3], wherein the amino acid corresponding to position 29 of SEQ ID NO: 1 is lysine (K).

[5] The Ig binding protein according to any one of items [1]-[4], wherein at least one domain comprises or consists of an amino acid sequence of any one of SEQ ID NOs: 4-36 and 40-49. In various embodiments, the Ig binding protein comprises an amino acid sequence of any of SEQ ID NOs: 4-9, 20-36, and 40-49.

or an amino acid sequence with at least 89.5% identity thereto to any of SEQ ID NO: 4-36, 40-49.

[6] The Ig binding protein according to any one of items [1]-[5], wherein said protein binds to one or more of IgG₁, IgG₂, IgG₄, IgM, IgA, Ig fragments, Fc fragments, Fab fragments, fusion proteins comprising an Ig region, and conjugates comprising an Ig region. In various embodiments, the Ig binding protein is binding to proteins comprising an Fc region or is binding to Fc fragments.

[7] The Ig binding protein according to any one of items [1]-[6], wherein the protein comprises 2, 3, 4, 5, or 6 domains linked to each other.

[8] The Ig binding protein according to item [7], wherein the protein is a homo-multimer or a hetero-multimer. In some embodiments, the Ig binding protein is a dimer comprising the sequence of SEQ ID NO: 37, SEQ ID NO: 50, or SEQ ID NO: 51.

[9] The Ig binding protein according to any one of items [1]-[8], wherein the protein is immobilized to a solid support. In some embodiments, the Ig binding protein is immobilized to a solid support by a cysteine (C) at the position corresponding to position 43 or 46 of SEQ ID NO: 1.

[10] The Ig binding protein according to any one of items [1]-[9], wherein the Ig binding protein is stable under alkaline conditions, optionally for at least 20 h at 0.5 M NaOH.

[11] An affinity separation matrix comprising the Ig binding protein of any one of items [1] to [10] coupled to said affinity separation matrix.

[12] Use of the Ig binding protein of any one of items [1] to [10], or the affinity separation matrix of item [11] for affinity purification of any protein with affinity to the Ig binding protein.

[13] A method of affinity purification of a protein comprising an Ig sequence, the method comprising:
  a) providing a liquid that contains protein comprising an Ig sequence;
  b) providing an affinity separation matrix according to item [11] comprising at least one Ig binding protein of any one of items [1] to [10] coupled to said affinity separation matrix of item [11];
  c) contacting said affinity separation matrix with the liquid under conditions that permit binding of the at least one Ig binding protein according to any one of items [1]-[10] to a protein comprising an Ig sequence; and
  d) eluting said protein comprising an Ig sequence from said affinity purification matrix, thereby obtaining an eluate containing said immunoglobulin.

[14] The method according to item [13], wherein in step (d) more than 95% of the protein comprising the Ig sequence is eluted at pH 3.7 or higher from the affinity separation matrix comprising the Ig binding protein according to any of items [1]-[10]. In various embodiments, in step (d) more than 95% of the protein comprising the Ig sequence is eluted at pH 4.5 from the affinity separation matrix comprising the Ig binding protein according to any of items [1]-[10].

[15] The method according to any of items [13]-[14], comprising the additional step (e) of cleaning the affinity purification matrix with an alkaline cleaning liquid, optionally wherein at least 90% of the Ig binding protein retains Ig binding activity after incubation for at least 20 h at 0.5 M NaOH.

[16] The present invention provides an Immunoglobulin (Ig) binding domain having at least 80% amino acid identity to SEQ ID NO: 1 (cs26), wherein the amino acid corresponding to positions 4, 6, or 8 of SEQ ID NO: 1 is isoleucine (I) or leucine (L) or an aromatic amino acid. Preferably, the Immunoglobulin (Ig) binding domain is/corresponds to an Ig binding protein having at least 80% amino acid identity to SEQ ID NO: 1 (cs26), wherein the amino acid corresponding to positions 4, 6, or 8 of SEQ ID NO: 1 is isoleucine (I) or leucine (L) or an aromatic amino acid, as described under item [1] above.

This summary of the invention does not necessarily describe all features of the present invention. Other embodiments will become apparent from a review of the ensuing detailed description.

BRIEF DESCRIPTION OF THE FIGURES

FIG. 1. Amino acid sequences of novel Ig binding proteins. The numbers in the top row refer to the corresponding amino acid position in the Ig binding protein.

FIG. 2, 3, 4. Caustic stability of Ig binding proteins coupled to Praesto Epoxy 85 resin (coupling 18 h at 35° C.) after incubation for 20 h with 0.5 M NaOH. SBC determination with 6 mg Gammanorm. Coupling of variants and parent to the resin via Cysteine located in the third helix (position 43C).

FIG. 2. Variants 8I, 8V, 8F, 8W, 8L, and 8Y show significantly improved remaining activity after long term incubation at alkaline conditions, in comparison to the parent molecule (cs26).

FIG. 3. Variants 4F and 4W show improved remaining activity after long term incubation at alkaline conditions, in comparison to the parent molecule (cs26).

FIG. 4. Variants 6F, 6I, 6L, 6V, 6W, 6Y, 6R show improved remaining activity after long term incubation at alkaline conditions, in comparison to the parent molecule (cs26).

FIG. 5. Elution profile of Belimumab from affinity ligand (SEQ ID NO: 51). The antibody was injected onto the column with immobilized affinity ligand (SEQ ID NO: 51) and eluted with linear pH gradient from pH 6.0 to 2.0. The pH of the elution peak maximum was used as readout.

FIG. 6. DBC10% determination of affinity ligand SEQ ID NO: 51. Belimumab was loaded onto resin with immobilized affinity ligand SEQ ID NO: 51 ("ID51" in the figure) until 10% target breakthrough. Elution of Belimumab was performed at pH 4.8 followed by CIP at pH 1.7. The chromatogram shows complete elution of bound Belimumab at pH 4.8.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only and is not intended to limit the scope of the present invention which may be limited only by the appended claims. Unless defined otherwise, all technical and scientific terms used herein have the same meanings as commonly understood by one of ordinary skill in the art to which this invention belongs.

Preferably, the terms used herein are consistent with the definitions provided in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

The term "about", as used herein, encompasses the explicitly recited amounts as well as deviations therefrom of ±10%. More preferably, a deviation of 5% is encompassed by the term "about".

Several documents (for example: patents, patent applications, scientific publications, manufacturer's specifications etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

In the context of the present invention, the term "Ig binding protein" or "immunoglobulin-binding protein" is used to describe proteins that are capable to specifically bind to an immunoglobulin. Further, in the context of the present invention, the term "Ig binding domain" or "immunoglobulin-binding domain" is used to describe proteins that are capable to specifically bind to an immunoglobulin. The Ig binding proteins or Ig binding domains of the present invention are sometimes referred to herein as ligands of the invention. The "immunoglobulin" or "Ig" as understood herein can include, but is not necessarily limited to, mammalian IgG, such as for example human $IgG_1$, human $IgG_2$, human $IgG_4$, mouse IgG, rat IgG, goat IgG, bovine IgG, guinea pig IgG, rabbit IgG; human IgM, human IgA; and an immunoglobulin fragment comprising a Fc region (also referred to as "Fc fragment" or "Fc") and/or an immunoglobulin fragment comprising a Fab region (also referred to as "Fab fragment" or "Fab"). The Ig binding proteins are capable of binding to entire immunoglobulins, and to Ig fragments comprising a Fc region and/or Ig fragments comprising a Fab region. The definition "immunoglobulin" as understood herein includes fusion proteins comprising an immunoglobulin, fragment of an immunoglobulin comprising a Fc region (Fc fragment), fragment of an immunoglobulin comprising a Fab region (Fab fragment), fusion proteins comprising a fragment of an immunoglobulin comprising a Fc region, fusion proteins comprising a fragment of an immunoglobulin comprising a Fab region, conjugates comprising an Ig or an Ig fragment comprising a Fc region (Fc fragment), and conjugates comprising an Ig fragment comprising a Fab region (Fab fragment).

As will be appreciated by a person of ordinary skill in the art, the terms "immunoglobulin" and "antibody" may be used interchangeably herein. Any definitions disclosed herein concerning the term "immunoglobulin" apply to the term "antibody" accordingly.

The term "binding" according to the invention preferably relates to a specific binding. "Specific binding" means that an Ig binding protein or an Ig binding domain binds stronger to an immunoglobulin for which it is specific compared to the binding to another non-immunoglobulin target.

The term "binding activity" refers to the ability of an Ig binding protein or Ig binding domain of the invention to bind to immunoglobulin. For example, the binding activity can be determined before and/or after alkaline treatment. The terms (immunoglobulin) "binding activity" and "binding capacity" may be used interchangeably herein. The binding activity can be determined for an Ig binding protein or for an Ig binding protein coupled to a matrix, i.e., for an immobilized Ig binding protein. Also, the binding activity can be determined for an Ig binding domain or for an Ig binding domain coupled to a matrix, i.e., for an immobilized Ig binding domain. The term "artificial" refers to an object that is not naturally occurring, i.e. the term refers to an object that has been produced or modified by man. For example, a polypeptide or polynucleotide sequence that has been generated by man (e.g. for example in a laboratory by genetic engineering, by shuffling methods, or by chemical reactions, etc.) or intentionally modified is artificial.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first protein and a second protein. In the context of the present invention, the term $K_D$ is particularly used to describe the binding affinity between an Ig binding protein or an Ig binding domain and an immunoglobulin. An Ig binding protein or Ig binding domain of the invention is considered to bind to an immunoglobulin, if it has a dissociation constant $K_D$ to immunoglobulin of at least 500 nM or less, or preferably 100 nM or less, more preferably 50 nM or less, even more preferably 10 nM or less.

The terms "protein" and "polypeptide" refer to any linear molecular chain of two or more amino acids linked by peptide bonds and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Ig binding proteins comprising two or more protein domains also fall under the definition of the term "protein" or "polypeptides".

The terms "alkaline stable" or "alkaline stability" or "caustic stable" or "caustic stability" (also abbreviated as "cs" herein) may be used interchangeably herein and refer to the ability of the Ig binding protein or Ig binding domain of the invention to withstand alkaline conditions without significantly losing the ability to bind to immunoglobulins. The skilled person in this field can easily test alkaline stability by incubating an Ig binding protein or Ig binding domain with, for example, sodium hydroxide solutions, e.g., as described in the Examples, and subsequent testing of the binding capacity or binding activity to immunoglobulin by routine experiments known to someone skilled in the art, for example, by chromatographic approaches. The alkaline stability may be determined by coupling the Ig binding protein or Ig binding domain of the invention to a surface plasmon resonance (SPR) sensor chip, and assaying the binding capacity or binding activity for immunoglobulin before and after exposure to an alkaline solution. The alkaline treatment can be performed, for instance, in 0.5 M NaOH for an extended period of time, e.g., at least 20 h.

Ig binding proteins or Ig binding domains of the invention as well as matrices comprising Ig binding proteins or Ig binding domains of the invention exhibit an "increased" or "improved" alkaline stability, meaning that the molecules and matrices incorporating said Ig binding proteins or Ig binding domains are stable under alkaline conditions for an extended period of time relative to a reference. In various embodiments, the reference may be the parent molecule cs26 having the sequence of any one of SEQ ID NOs: 1-3, preferably the sequence of SEQ ID NO: 3 (cs26 43C). In various other embodiments, the reference may be the parent molecule cs26 of any of SEQ ID NOs: 1-3 having a substitution D8E (Asp8Glu), preferably the parent molecule cs26 of SEQ ID NO: 3 having a substitution D8E (Asp8Glu).

The term "variant" as used herein includes an amino acid sequence of an Ig binding protein or Ig binding domain that differs from another amino acid sequence by at least one amino acid substitution, deletion or insertion. These modifications may be generated by genetic engineering or by chemical synthesis or chemical reactions carried out by man.

The term "conjugate" as used herein relates to a molecule comprising or essentially consisting of at least a first protein attached chemically to other substances such as to a second protein or a non-proteinaceous moiety.

The term "modification" or "amino acid modification" refers to an exchange, a deletion, or an insertion of an amino acid at a particular position in a polypeptide sequence by another amino acid. Given the known genetic code, and recombinant and synthetic DNA techniques, the skilled scientist can readily construct DNAs encoding the amino acid variants.

The term "substitution" or "amino acid substitution" refers to an exchange of an amino acid at a particular position in a polypeptide sequence by another amino acid. The term "deletion" or "amino acid deletion" refers to the removal of an amino acid at a particular position in a polypeptide sequence.

The term "insertions" or "amino acid insertion" refers to the addition of amino acids to the polypeptide sequence.

Throughout this description, the amino acid residue position numbers are designated as corresponding to those for example in SEQ ID NO: 1.

The term "amino acid sequence identity" refers to a quantitative comparison of the identity (or differences) of the amino acid sequences of two or more proteins. "Percent (%) amino acid sequence identity" or "percent identical" or "percent identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. In various embodiments, the term "sequence identity" means that two (nucleotide or) amino acid sequences, when optimally aligned, such as by the programs GAP or BESTFIT using default gap weights, share at least 70% sequence identity, or at least 80% sequence identity, or at least 85% sequence identity, or at least 90% sequence identity, or at least 95% sequence identity or more.

To determine the sequence identity, the sequence of a query protein is aligned and compared to the sequence of a reference protein. Methods for sequence alignment and sequence comparison algorithms are well known in the art. For example, for determining the extent of an amino acid sequence identity of an arbitrary polypeptide relative to the reference amino acid sequence, the SIM Local similarity program is preferably employed. For multiple alignment analysis, ClustalW as known to someone skilled in the art is preferably used.

The extent of sequence identity is generally calculated with respect to the total length of the unmodified sequence. As used herein, the phrases "percent identical" or "percent (%) amino acid sequence identity" or "percent identity", in the context of two polypeptide sequences, refer to two or more sequences or subsequences that have in some embodiments at least 89.5%, in some embodiments at least 91%, some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments 100% amino acid residue identity, when compared and aligned for maximum correspondence, as measured using one of the following sequence comparison algorithms or by visual inspection. For clarity reasons, for example a sequence with at least 89.5% identity includes all sequences with identities higher than 89.5% identity, e.g. embodiments with at least 89.6%, at least 90%, at least 91%, at least 92%, at least 93%, at least 94%, at least 95%, at least 96%, at least 97%, at least 98%, at least 99%, or 100% amino acid identity.

The percent identity exists in some embodiments over a region of at least 52 residues, in some embodiments over a region of at least 53 residues, in some embodiments over a region of at least 54 residues, in some embodiments over a region of at least 55 residues, in some embodiments over a region of at least 56 residues, in some embodiments over a region of at least 57 residues, and in some embodiments over a region of at least 58 residues.

The term "fused" means that polypeptide components or units are linked by peptide bonds, either directly or via peptide linkers. In various embodiments, the term "fused" may mean that polypeptide components or units are linked by a non-peptide linker, e.g., through chemical conjugation.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide. In various embodiments, a fusion protein is created through joining of two or more polypeptides via a non-peptide linker, e.g., through chemical conjugation. In various embodiments, a dimer of an Ig binding protein or Ig binding domain of the present invention may be considered as a "fusion protein".

As used herein, the term "linker" refers in its broadest meaning to a molecule that covalently joins at least two other molecules. In typical embodiments of the present invention, a "linker" is to be understood as a moiety that connects an Ig binding protein or Ig binding domain with at least one further Ig binding protein or Ig binding domain, i.e. a moiety linking two protein domains to each other to generate a dimer or a multimer. In preferred embodiments, the "linker" is a peptide linker, i.e. the moiety linking the two binding proteins or binding domains is one single amino acid or a peptide comprising two or more amino acids. In various embodiments, a dimer or multimer of the present invention may comprise a linker joining two or more Ig binding proteins or Ig binding domains with each other.

The term "chromatography" refers to separation technologies which employ a mobile phase and a stationary phase to separate one type of molecules (e.g., immunoglobulins) from other molecules (e.g. contaminants or other immunoglobulins) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific binding affinity or binding capacity for the molecule to be purified. As understood in the context of the invention, affinity chromatography involves the addition of a (liquid) sample containing an immunoglobulin to a stationary phase which comprises a chromatography ligand, such as an Ig binding protein or Ig binding domain of the invention.

The terms "solid support" or "solid matrix" are used interchangeably herein, and in various embodiments are used for the stationary phase.

The terms "affinity matrix" or "affinity separation matrix" or "affinity chromatography matrix", as used interchangeably herein, refer to a matrix, e.g. a chromatographic matrix, onto which an affinity ligand e.g., an Ig binding protein or Ig binding domain of the invention is attached. The ligand (e.g., Ig binding protein or Ig binding domain) is capable of specific binding to a molecule of interest (e.g., an immunoglobulin as defined above) which is to be purified or removed from a mixture (in a liquid sample). As will be appreciated by a person of ordinary skill in the art, the terms "affinity matrix" or "affinity separation matrix" or "affinity chromatography matrix" describe the separation of a molecule of interest (in particular an immunoglobulin) by using an Ig binding protein or Ig binding domain of the invention. Accordingly, the terms "affinity matrix" or "affinity separation matrix" or "affinity chromatography matrix" or "separation matrix" may be used interchangeably herein.

The term "affinity purification" as used herein refers to a method of purifying immunoglobulins of interest as defined above from a liquid (sample) by binding immunoglobulins of interest as defined above to an Ig binding protein or Ig binding domain that is immobilized to a matrix. Thereby, all other components of the mixture except immunoglobulins of interest are removed. In various embodiments, said other components of the mixture may include, e.g., other immunoglobulins that are not of interest. In a further step, immunoglobulins of interest are eluted in purified form. The terms "affinity purification" or "affinity chromatography purification" or "affinity separation" or "affinity chromatography separation" may be used interchangeably herein.

EMBODIMENTS OF THE INVENTION

The present invention will now be further described. In the following passages different embodiments of the invention are defined in more detail. Each embodiment defined below may be combined with any other embodiments unless clearly indicated to the contrary. In particular, any feature indicated as being preferred or advantageous may be combined with any other feature or features indicated as being preferred or advantageous.

The present invention provides an Ig binding domain, which corresponds to an Ig binding protein having at least 80% amino acid identity to SEQ ID NO: 1 (cs26), wherein the amino acid corresponding to position 8 of SEQ ID NO: 1 is isoleucine (I) or leucine (L) or valine (V) or an aromatic amino acid, which may be any of tryptophan (W), phenylalanine (F), or tyrosine (Y). Preferably, the amino acid corresponding to position 8 of SEQ ID NO: 1 is isoleucine (I) or leucine (L), more preferably the amino acid corresponding to position 8 of SEQ ID NO: 1 is isoleucine (I). In various embodiments, the amino acid corresponding to position 14 of SEQ ID NO: 1 is histidine (H), and/or the amino acid corresponding to position 29 of SEQ ID NO: 1 is lysine (K). The Ig binding domain may further have a cysteine (C) residue at the position corresponding to position 43 or 46 of SEQ ID NO: 1. The Ig binding domain is stable under alkaline conditions of 0.5 M NaOH for at least 20 h. As described elsewhere herein, an Ig binding protein of the invention comprises one or more such Ig binding domains.

In one embodiment, the Ig binding protein comprises one or more domains, wherein at least one domain comprises or essentially consists of or consists of an amino acid substitution at one or more amino acids corresponding to positions 4, 6, or 8 of SEQ ID NO: 1, the substitution at the amino acid corresponding to position 4, 6, or 8 of SEQ ID NO: 1 is an amino acid selected from the group of Iso (I), Leu (L), Tyr (Y), Phe (F), Val (V), or Trp (W), and wherein the amino acid sequence of the Ig binding protein is at least 80% identical to SEQ ID NO: 1.

In one embodiment, the Ig protein comprises one or more domains, wherein at least one domain comprises an amino acid substitution at an amino acid corresponding to position 8 of SEQ ID NO: 1 selected from the group of highly hydrophobic amino acids with branched side chains (Iso, Leu, Val), or aromatic amino acids (Tyr, Phe, or Trp), and wherein the amino acid sequence of the Ig binding protein is at least 80% identical to SEQ ID NO: 1. In some embodiments, the amino acid corresponding to position 8 of SEQ ID NO: 1 is isoleucine (I) or tyrosine (Y). In some preferred embodiments, the amino acid corresponding to position 8 of SEQ ID NO: 1 (or functionally equivalent proteins) is isoleucine (I). In various embodiments, Isoleucine (I) in a position corresponding to position 8 of SEQ ID NO: 1 improves the Ig binding capacity and caustic stability. Further, an isoleucine in position corresponding to position 8 of SEQ ID NO: 1 (or functionally equivalent proteins) might improve the expression of the protein. For an Ig binding ligand of the present invention with high binding capacity and caustic stability suitable for uses in affinity chromatography, it is important that the amino acid in position 8 is not selected from any one of arginine (R), serine (S), threonine (T), or alanine (A) (see FIG. 2). The present invention demonstrates an improved caustic stability over these substitutions at position 8 of SEQ ID NO: 1 as well as over the substitution D8E (Asp8Glu). Accordingly, in various embodiments of the present invention the amino acid corresponding to position 8 of SEQ ID NO: 1 is not glutamic acid (E).

In some embodiments, the Ig binding protein or Ig binding domain of the invention is selected from the following (1) to (3): (1) a protein comprising an amino acid sequence corresponding to SEQ ID NO: 1 wherein an amino acid residue at the 8th position is substituted by Ile, Leu, Val, or an aromatic amino acid; (2) a protein comprising an amino acid sequence specified in the (1) further having deletion, substitution and/or addition of one or more amino acid residues in a position other than the 8th position; (3) a protein comprising an amino acid sequence having a sequence identity of at least 80% or more with the amino acid sequence specified in the (1), provided that the amino acid substitution specified in the (1) at the 8th position is not further mutated in (3).

The present invention further provides an Ig protein comprising an amino acid substitution at a position corresponding to position 4 of SEQ ID NO: 1 selected from the group of from the group of highly hydrophobic amino acids with branched side chains (Iso, Leu), or aromatic amino acids (Tyr, Phe, or Trp), and wherein the amino acid sequence of the Ig binding protein is at least 80% identical to SEQ ID NO: 1. In preferred embodiments, the amino acid corresponding to position 4 of SEQ ID NO: 1 is tryptophan (W) or phenylalanine (F). Aromatic amino acids such as W or F in a position corresponding to position 4 of SEQ ID NO: 1 improve the binding capacity and caustic stability of the ligand in affinity chromatography. For an Ig binding ligand with high binding capacity and caustic stability suitable for uses in affinity chromatography, it is important that the amino acid in position 4 is not selected from arginine (R), serine (S), threonine (T), alanine (A), or valine (V) (see FIG. 3).

In some embodiments, the protein of the invention is selected from the following (1) to (3): (1) a protein comprising an amino acid sequence corresponding to SEQ ID NO: 1 wherein an amino acid residue corresponding to the 4th position is substituted by Ile, Leu, or an aromatic amino acid; (2) a protein comprising an amino acid sequence specified in the (1) further having deletion, substitution and/or addition of one or more amino acid residues in a position other than the 4th position; (3) a protein comprising an amino acid sequence having a sequence identity of at least 80% or more with the amino acid sequence specified in the (1), provided that the amino acid substitution specified in the (1) at the 4th position is not further mutated in (3).

The present invention further provides an Ig protein comprising an amino acid substitution at a position corresponding to position 6 of SEQ ID NO: 1 selected from selected from the group of Iso, Leu, Tyr, Phe, or Trp, and wherein the amino acid sequence of the Ig binding protein is at least 80% identical to SEQ ID NO: 1. In preferred embodiments, the amino acid corresponding to position 6 of SEQ ID NO: 1 is isoleucine (I), tryptophan (W), or tyrosine (Y), or leucine (L). Aromatic amino acids such as Trp (W) or Tyr (Y), or amino acids selected from Iso (I) or Leu (L) in a position corresponding to position 6 of SEQ ID NO: 1 improve the binding capacity and caustic stability of the ligand in affinity chromatography. For an Ig binding ligand with high binding capacity and caustic stability suitable for uses in affinity chromatography, it is important that the amino acid in position 6 is not selected from valine (V), serine (S) or alanine (A) (see FIG. 4).

In some embodiments, the protein of the invention is selected from the following (1) to (3): (1) a protein comprising an amino acid sequence of SEQ ID NO: 1 wherein an amino acid residue at the 6th position is substituted by Ile, Leu, or an aromatic amino acid; (2) a protein comprising an amino acid sequence specified in the (1) further having deletion, substitution and/or addition of one or more amino acid residues in a position other than the 6th position; (3) a protein comprising an amino acid sequence having a sequence identity of at least 80% or more with the amino acid sequence specified in the (1), provided that the amino acid substitution specified in the (1) at the 6th position is not further mutated in (3).

The surprising advantage of the Ig binding proteins and Ig binding domains of the invention is the stability under extreme conditions such as high pH (pH 13 and higher) without losing Ig binding properties. The Ig binding proteins and Ig binding domains as described herein demonstrate alkali stability for a prolonged period of time without impairing the Ig-binding properties (see FIGS. 2, 3, 4 and Examples). Further, they are stable at low pH without significantly losing Ig binding properties. The alkali stability feature is particularly important for chromatography approaches with cleaning procedures using alkaline solutions with high NaOH concentrations to remove contaminants on the matrix so for example that the matrix can be used several times. In addition to high caustic stability, Ig binding proteins show high coupling efficiencies, as shown in the Examples.

Further, an important step in affinity chromatography is the elution of the protein of interest, particular an immunoglobulin of interest, that is bound to the Ig binding protein or Ig binding domain of the invention. This step is usually done at low pH. The affinity ligands of the invention do not lose binding properties to Ig after this treatment, while elution of the protein of interest is possible at low pH.

In some circumstances, it is important to have conditions for the elution of antibodies (immunoglobulins) from the affinity ligand at pH between 3.7 higher, such as pH 4.3 and above, for example, up to pH 5.5. In order to improve characteristics of the ligands of the invention, further modifications can be made to the ligands described above. In some embodiments, one or more amino acid(s) corresponding to position 10, 14, 16, 17, 18, or 28 of SEQ ID NO: 1 are selected from the group of histidine (H) or acidic amino acids selected from aspartate (D) or glutamate (E). In some embodiments, the amino acid corresponding to position 14 of SEQ ID NO: 1 is H. In some embodiments, the amino acid corresponding to position 16 of SEQ ID NO: 1 is H. In other embodiments, the amino acid corresponding to position 28 of SEQ ID NO: 1 is H. In some embodiments, the amino acid corresponding to position 28 of SEQ ID NO: 1 is E. In other embodiments, the amino acid corresponding to position 9 of SEQ ID NO: 1 is H. In some embodiments, the amino acid corresponding to position 10 of SEQ ID NO: 1 is H. Ligands of the invention with His (H), Asp (D), or Glu (E) in positions corresponding to positions 10, 14, 16, 17, 18, or 28 of SEQ ID NO: 1 weaken the Fc binding affinity and allow elution of the bound Ig protein of interest at pH higher than 4.0 or even pH 4.3, up to pH 5.5.

It has surprisingly been found that an Ig binding protein or Ig binding domain of the present invention comprising a histidine (H) at the position corresponding to position 14 of SEQ ID NO: 1 or a histidine (H) at the position corresponding to position 16 of SEQ ID NO: 1 is particularly suitable for elution of Ig molecules of interest from the immobilized ligand at mild pH conditions (up to pH 5.5)(see Table 3). This feature is particularly useful for isolating immunoglobulins, in particular Ig having an Fc region, using separation matrices, wherein the elution step has to be carried out at mild acidic conditions higher than pH 3.7, in particular in the range of pH 4.0 up to and including pH 5.5.

In some embodiments, the Ig binding protein or Ig binding domain is selected from the following (1) to (3): (1) a protein comprising an amino acid sequence corresponding to SEQ ID NO: 1 wherein the amino acid residue corresponding to the 8th position is Ile, Leu, Val, or an aromatic amino acid; (2) a protein comprising an amino acid sequence specified in the (1) wherein the amino acid residue corresponding to the $10^{th}$, $14^{th}$, $16^{th}$, $17^{th}$, $18^{th}$, or $28^{th}$ position is His, Asp, or Glu, preferably wherein the amino acid corresponding to position 14 is His, the amino acid corresponding to position 16 is His, the amino acid corresponding to position 10 is Asp or His, the amino acid corresponding to position 17 is His, the amino acid corresponding to position 18 is Glu, or the amino acid corresponding to position 28 is His or Glu, more preferably wherein the amino acid corresponding to position 14 is His, (3) a protein comprising an amino acid sequence having a sequence identity of at least 80% or more with the amino acid sequence specified in the (1), provided that the amino acid specified in (1) corresponding to the 8th position and the amino acid in the (2) corresponding to the $10^{th}$, $14^{th}$, $16^{th}$, $17^{th}$, $18^{th}$, or $28^{th}$ position is not further mutated in (3).

Further modifications can be introduced to the protein to modify certain properties for affinity chromatography. For example, a cysteine can be added to the C-terminus. Alternatively, a cysteine can be introduced at a position within helix 3 of the protein, for example, in position 43 or position 46, to enable efficient coupling to the matrix.

In another embodiment, the position corresponding to position 29 might be exchanged in order to lower the binding of Ig (by eliminating Fab-VH3 binding) and improve elution properties at higher pH values. In some embodiments, the amino acid corresponding to position 29 of SEQ ID NO: 1 is Lys (K). In some embodiments, the resulting ligand of the invention has at least 80% identity to SEQ ID NO: 1.

In some embodiments, the Ig binding protein or Ig binding domain is selected from the following (1) to (3):

(1) protein comprising an amino acid sequence corresponding to SEQ ID NO: 1 wherein the amino acid residue corresponding to the 8th position is Ile, Leu, Val, or an aromatic amino acid;

(2) a protein comprising an amino acid sequence specified in (1) wherein the amino acid residue corresponding to the $10^{th}$, $14^{th}$, $16^{th}$, $17^{th}$, $18^{th}$, or $28^{th}$ position is His, Asp, or Glu, preferably wherein the amino acid corresponding to position 14 is His, the amino acid corresponding to position 16 is His, the amino acid corresponding to position 10 is Asp or His, the amino acid corresponding to position 17 is His, the amino acid corresponding to position 18 is Glu, or the amino acid corresponding to position 28 is His or Glu, more preferably wherein the amino acid corresponding to position 14 is His;

(3) a protein comprising an amino acid sequence specified in the (1) wherein the amino acid residue corresponding to the 29th position is Lys;

(4) a protein comprising an amino acid sequence having a sequence identity of at least 80% or more with the amino acid sequence specified in the (1), provided that the amino acids specified in the (1), (2), and (3) are not further mutated in (4).

Preferred Ig binding domains. In various embodiments, the Ig binding domain comprises or consists of an amino acid sequence of any one of SEQ ID NOs: 4-36 and 40-49, or an amino acid with at least 80%, at least 85%, at least 89.5%, at least 90%, at least 91%, at least 92%, at least 93%, at least 94%, at least 95%, at least 96%, at least 97%, at least 98%, or at least 99% identity thereto. In various embodiments, the Ig binding domain comprises or essentially consists of or consists of an amino acid sequence of any of SEQ ID NOs: 4-36 and 40-49, or an amino acid with at least 95%, at least 96%, at least 97%, at least 98%, or at least 99% identity to any of SEQ ID NOs: 4-36 and 40-49.

Preferred Ig binding proteins. In some embodiments, the Ig binding protein comprises one or more binding domains wherein at least one domain comprises or consists of an amino acid sequence of any one of SEQ ID NOs: 4-36 and 40-49, or an amino acid with at least 80%, at least 85%, at least 89.5%, at least 90%, at least 91%, at least 92%, at least 93%, at least 94%, at least 95%, at least 96%, at least 97%, at least 98%, or at least 99% identity thereto. In some embodiments, the Ig binding protein comprises one or more domains, wherein at least one domain comprises or essentially consists of or consists of an amino acid sequence of any of SEQ ID NOs: 4-36 and 40-49, or an amino acid with at least 95%, at least 96%, at least 97%, at least 98%, or at least 99% identity to any of SEQ ID NOs: 4-36 and 40-49.

Affinity to Immunoglobulin. All Ig binding proteins or Ig binding domains as described herein bind to Immunoglobulin with a dissociation constant $K_D$ preferably below 200 nM, or below 100 nM, even more preferably 10 nM or less. In some embodiments, the Ig binding protein or Ig binding domain binds to $IgG_1$, $IgG_2$, $IgG_4$, IgM, IgA, Ig fragments, Fc fragments, Fab fragments, fusion proteins comprising an Ig region, and conjugates comprising an Ig region with a dissociation constant $K_D$ preferably below 200 nM, or below 100 nM, even more preferably 10 nM or less. Methods for determining binding affinities or binding capacities of Ig binding proteins or domains, i.e. for determining the dissociation constant $K_D$, are known to a person of ordinary skill in the art and can be selected for instance from the following methods known in the art: Surface Plasmon Resonance (SPR) based technology, kinetic exclusion analysis (KinExA assay), Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Some of the methods are described further in the Examples. Typically, the dissociation constant $K_D$ is determined at 20° C., 25° C., or 30° C. If not specifically indicated otherwise, the $K_D$ values recited herein are determined at 22° C.+/−3° C. by surface plasmon resonance spectroscopy. In one embodiment, the Ig binding protein has a dissociation constant $K_D$ to human $IgG_1$ in the range between 0.1 nM and 100 nM, preferably between 0.1 nM and 50 nM.

High alkaline stability of Ig binding proteins. The Ig binding proteins and Ig binding domains of the invention provide surprisingly particularly good alkaline stability, as shown in the Examples and in the Figures, in addition to high dynamic binding capacities (DBC). The alkaline stability of the Ig binding protein or Ig binding domain is determined by comparing the loss in Ig binding activity. In some embodiments, the alkaline liquid comprises 0.1-1.0 M NaOH or KOH, preferably 0.25-0.5 M NaOH or KOH. Due to the high alkaline stability of the Ig binding proteins and Ig binding domains of the invention, an alkaline liquid with pH higher than 13 can be used for cleaning affinity matrices with immobilized Ig binding proteins or immobilized Ig binding domains of the invention. In some embodiments, the alkaline stability of the Ig binding protein or Ig binding domain is determined by comparing the loss in Ig binding activity after at least 20 h incubation in 0.5 M NaOH (see FIG. 2, FIG. 3, FIG. 4 and Examples). In some embodiments, the alkaline stability of the Ig binding protein or Ig binding domain is determined by comparing the loss in Ig binding activity after very long incubation in alkaline solution, e.g. for at least 2 days (at least 48 h) incubation in 0.5 M NaOH (see Examples), reflecting an extraordinary stability of the Ig binding proteins as described herein.

The Ig binding proteins and Ig binding domains of the invention are stable under alkaline conditions, in particular under alkaline conditions of 0.5 M NaOH for at least 20 h. In various embodiments, the Ig binding protein or Ig binding domain of the invention is stable under alkaline conditions, in particular under alkaline conditions of 0.5 M NaOH for at least 24 h. In preferred embodiments, the Ig binding protein or Ig binding domain of the invention is stable under alkaline conditions, in particular under alkaline conditions of 0.5 M NaOH for at least 48 h, more preferably for at least 50 h.

The Ig binding proteins and Ig binding domains of the invention are alkaline-stable ligands for immunoglobulins. The Ig binding proteins and Ig binding domains of the invention retain binding capacity (or binding affinity) for immunoglobulin after exposure to 0.5 M NaOH for at least 20 h. As further described herein, the Ig binding proteins and Ig binding domains of the invention retain at least 85% or at least 90% binding capacity for immunoglobulin after exposure to alkaline conditions as described herein. In further preferred embodiments, the Ig binding proteins and Ig binding domains of the invention retain at least 94% binding capacity for immunoglobulin after exposure to alkaline conditions (0.5 M NaOH for at least 20 h or 24 h), preferably after exposure to 0.5 M NaOH for at least 48 h, more preferably after exposure to 0.5 M NaOH for at least 50 h. In various embodiments, the Ig binding proteins and Ig binding domains of the invention retain binding capacity for immunoglobulin as described above when immobilized to a solid support, preferably to a solid support of an affinity separation matrix.

As further described herein, the Ig binding proteins and Ig binding domains of the invention are typically stable under alkaline conditions at room temperature. The term room temperature may include temperatures between 15° C. and 25° C., more specifically temperatures between 20° C. and 25° C. In various embodiments, the Ig binding protein or Ig binding domain of the invention is stable under alkaline conditions at 22° C.±3° C.

In various embodiments, the alkaline stability of the Ig binding protein or Ig binding domain as described above means alkaline stability of the Ig binding protein or Ig binding domain immobilized to a solid support, preferably to a solid support of an affinity separation matrix. Hence, in various embodiments, the alkaline stability of the Ig binding protein or Ig binding domain is determined by comparing the loss in Ig binding activity or Ig binding capacity of the Ig binding protein or Ig binding domain when immobilized to a solid support, preferably to a solid support of an affinity separation matrix. Hence, in other embodiments, the alkaline stability of the Ig binding protein or Ig binding domain is determined by comparing the Ig binding activity of the Ig binding protein or Ig binding domain to a reference protein after alkaline treatment for a prolonged time when immobilized to a solid support (see FIGS. 2, 3, 4).

The binding capacity or binding affinity for immunoglobulin of the Ig binding protein or Ig binding domain of the present invention can be evaluated by a skilled person using methods well known in the art, in particular methods for determining the dissociation constant $K_D$ as described elsewhere herein. In various embodiments, the binding capacity or binding affinity for immunoglobulin of the Ig binding protein or Ig binding domain of the present invention is determined using Surface Plasmon Resonance (SPR) spectroscopy, as also described elsewhere herein. In other embodiments, the binding capacity or binding affinity for immunoglobulin of the Ig binding protein or Ig binding domain of the present invention is determined using kinetic exclusion analysis (KinExA assay), or enzyme-linked immunosorbent assay (ELISA), as described elsewhere herein.

The binding capacity or binding affinity for immunoglobulin of the Ig binding protein or Ig binding domain of the present invention can be assessed for each candidate ligand before and after exposure to alkaline conditions as described herein.

Multimers. In one embodiment, the Ig binding protein comprises 1, 2, 3, 4, 5, or 6 Ig binding domains linked to each other, i.e. the Ig binding protein can be, for example, a monomer, a dimer, a trimer, a tetramer, a pentamer, or a hexamer. A multimer may comprise two, three, four, or even more binding domains. Multimers of the invention are fusion proteins generated artificially, generally by recombinant DNA technology well-known to a skilled person.

In some embodiments, the multimer is a homo-multimer, e.g. the amino acid sequences of all Ig binding domains of the Ig binding protein are identical. In some embodiments, the multimer is a hetero-multimer, e.g. at least one Ig binding domain has a different amino acid sequence than the other Ig binding domains within the Ig-binding protein.

A multimer may comprise two or more Ig binding domains, wherein said Ig binding domains preferably comprise or essentially consist of an amino acid sequence as described above. In some embodiments, the multimer is a dimer. The present invention provides dimers comprising monomers of any of SEQ ID NOs: 4-36 and 40-49. In various embodiments, an Ig binding protein of the invention is a dimer comprising two Ig binding domains, wherein each of the two Ig binding domains corresponds to an Ig binding protein having at least 80% amino acid identity to any one of SEQ ID NOs: 4-36 and 40-49, wherein the dimeric Ig binding protein is stable under alkaline conditions. In preferred embodiments, an Ig binding protein of the invention is a dimer comprising two Ig binding domains, wherein each of the two Ig binding domains corresponds to an Ig binding protein having at least 80% amino acid identity to any one of SEQ ID NOs: 4-9, 20-36, and 40-49, wherein the amino acid corresponding to position 8 of SEQ ID NOs: 4-9, 20-36, and 40-49 is isoleucine (I) or leucine (L) or valine (V) or an aromatic amino acid (Y, F, or W), and wherein the dimeric Ig binding protein is stable under alkaline conditions of 0.5 M NaOH for at least 20 h. In more preferred embodiments, a dimeric Ig binding protein of the invention comprises an Ig binding domain corresponding to an Ig binding protein having at least 80% amino acid identity to any one of SEQ ID NOs: 4-5, 20-36, and 40-49, wherein the amino acid corresponding to position 8 of SEQ ID NOs: 4-5, 20-36 and 40-49 is isoleucine (I), and wherein the dimeric Ig binding protein is stable under alkaline conditions of 0.5 M NaOH for at least 20 h. In more preferred embodiments, a dimeric Ig binding protein of the invention comprises an Ig binding domain corresponding to an Ig binding protein having at least 80% amino acid identity to any one of SEQ ID NOs: 4-5, 20-36, and 40-49, wherein the amino acid corresponding to position 8 of SEQ ID NOs: 4-5, 20-36 and 40-49 is isoleucine (I), and wherein the dimeric Ig binding protein is stable under alkaline conditions of 0.5 M NaOH for at least 20 h and wherein the dimeric Ig binding protein allows elution of the target at mild elution conditions of an pH of at least 4.0. In various embodiments, the N-terminal Ig binding domain of a dimer comprising two Ig binding domains has a cysteine (C) at the position corresponding to position 43 or 46 of SEQ ID NO: 1 or any of SEQ ID NOs: 4-36 and 40-49, respectively.

In further preferred embodiments, an Ig binding protein of the invention comprises two Ig binding domains, wherein one Ig binding domain corresponds to an Ig binding protein having at least 80% amino acid identity to SEQ ID NO: 4, and the other Ig binding domain corresponds to an Ig binding protein having at least 80% amino acid identity to SEQ ID NO: 5. Preferably, the domain based on SEQ ID NO: 5 is located upstream of the domain based on SEQ ID NO. 4. In further particularly preferred embodiments, an Ig binding protein of the invention comprises two Ig binding domains, wherein one Ig binding domain corresponds to an Ig binding protein having at least 80% amino acid identity to SEQ ID NO: 43, and the other Ig binding domain corresponds to an Ig binding protein having at least 80% amino acid identity to SEQ ID NO: 46. Preferably, the domain based on SEQ ID NO: 46 is located upstream of the domain based on SEQ ID NO: 43.

In some specific embodiments, the Ig binding protein is a dimer comprising the sequence of SEQ ID NO: 37, SEQ ID NO: 50, or SEQ ID NO: 51.

Linker. In various embodiments, the one or more Ig binding domains are directly linked to each other. In other embodiments, the one or more Ig binding domains are linked to each other with one or more linkers. Preferred in these typical embodiments are peptide linkers. This means that the peptide linker is one or more amino acids, e.g. an amino acid sequence, that connects a first Ig binding domain with a second Ig binding domain. The peptide linker is connected to the first Ig binding domain and to the second Ig binding domain by a peptide bond between the C-terminal and N-terminal ends of the domains, thereby generating a single, linear polypeptide chain. The length and composition of a linker may vary between at least one and up to about 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acids. It is preferred that the amino acid sequence of the peptide linker is stable against caustic conditions and proteases. Linkers should not destabilize the conformation of the domains in the Ig binding protein. Well-known are linkers that comprise or consist of small amino acids such as glycine and serine. The linkers can be glycine-rich (e.g., more than 50% of the residues in the linker can be glycine residues). Also preferred are linkers that comprise further amino acids. Other embodiments of the invention comprise linkers consisting of alanine, proline, and serine. Other linkers for the fusion of proteins are known in the art and can be used. In some embodiments, the multimer of Ig binding proteins comprises one or more linkers connecting the Ig binding domains wherein the linkers are identical or different.

Non-Ig binding proteins. In some embodiments, the Ig binding protein as described above further comprises at least one further polypeptide distinct from the Ig binding protein or Ig binding domain as disclosed. In various embodiments, the further polypeptide distinct from the Ig binding protein or Ig binding domain as disclosed herein might be a non-Ig-binding protein, for example but not limited to, a protein that does not bind to the Fc part of immunoglobulin. Accordingly, some embodiments encompass fusion proteins comprising one or two or more Ig binding protein(s) thereof as disclosed herein and one or two or more non-Ig-binding polypeptide(s). In some embodiments, a fusion protein may comprise one (or more) Ig binding protein(s) and/or one (or more) Ig binding domain(s) as disclosed herein fused to one (or more) non-Ig binding protein(s).

In some embodiments, a non-Ig binding protein has at least 89.5% or at least 91% or at least 93% or at least 95% or at least 96% or at least 98% or 100% identity to SEQ ID NO: 38 or SEQ ID NO: 39. SEQ ID NO: 39 is a non-Ig binding protein. SEQ ID NO: 39 has the same basic scaffold as SEQ ID NO: 1 but with modifications D8I, F13D, Y14K, I31R, L42A in SEQ ID NO: 1 which lead to the non-Ig binding property of SEQ ID NO: 39. The modification in position 8 to isoleucine results in improved biochemical properties such as high stability in the non-Ig binding protein, for example, in high stability under alkaline conditions. Accordingly, an isoleucine in a position corresponding to position 8 results in higher stability of proteins having a similar triple-helical structure as present in SEQ ID NO: 1, regardless of the function (i.e. Ig binding protein or non-Ig binding protein). Accordingly, the invention comprises further a protein comprising one or more domains, wherein at least one domain corresponds to a protein having at least 70% amino acid identity to SEQ ID NO: 1 (cs26), wherein the amino acid corresponding to position 8 of SEQ ID NO: 1 is isoleucine (I). In some embodiments, the protein comprising one or more domains, wherein at least one domain corresponds to a protein having at least 70% amino acid identity to SEQ ID NO: 1 (cs26), wherein the amino acid corresponding to position 8 of SEQ ID NO: 1 is isoleucine (I) is stable under alkaline conditions. In accordance with the above, the present invention provides a non-Immunoglobulin (Ig) binding protein comprising an amino acid sequence having at least 70%, preferably at least 80%, more preferably at least 85%, even more preferably at least 89.5%, identity to SEQ ID NO: 1, wherein the non-Ig binding protein comprises:

(i) an amino acid selected from any one of isoleucine (I), leucine (L), valine (V), or an aromatic amino acid (Tyr, Phe, or Trp), preferably any one of isoleucine (I), leucine (L), or an aromatic amino acid (Y, F, W), more preferably isoleucine (I) or leucine (L), even more preferably isoleucine (I), at the position corresponding to position 8 of SEQ ID NO: 1;

(ii) an aspartate (D) at the position corresponding to position 13 of SEQ ID NO: 1;

(iii) a lysine (K) or serine (S) at the position corresponding to position 14 of SEQ ID NO: 1;

(iv) an arginine (R) at the position corresponding to position 31 of SEQ ID NO: 1; and (v) an alanine (A) or leucine (L) at the position corresponding to position 42 of SEQ ID NO: 1. In some embodiments, the non-Ig binding protein is stable under alkaline conditions of 0.5 M NaOH for at least 20 h.

The present invention further provides a non-Ig binding protein having at least 89.5% or at least 91% or at least 93% or at least 95% or at least 96% or at least 98% or 100% sequence identity to the amino acid sequence of SEQ ID NO: 38 or SEQ ID NO: 39, wherein the non-Ig binding protein comprises:

(i) an amino acid selected from any one of isoleucine (I), leucine (L), valine (V), or an aromatic amino acid (Tyr, Phe, or Trp), preferably any one of isoleucine (I), leucine (L), or an aromatic amino acid (Y, F, W), more preferably isoleucine (I) or leucine (L), even more preferably isoleucine (I), at the position corresponding to position 8 of SEQ ID NO: 38 or 39;

(ii) an aspartate (D) at the position corresponding to position 13 of SEQ ID NO: 38 or 39;

(iii) a lysine (K) or a serine (S) at the position corresponding to position 14 of SEQ ID NO: 38 or 39;

(iv) an arginine (R) at the position corresponding to position 31 of SEQ ID NO: 38 or 39; and (v) an alanine (A) or a leucine (L) at the position corresponding to position 42 of SEQ ID NO: 38 or 39. In some embodiments, the non-Ig binding protein is stable under alkaline conditions of 0.5 M NaOH for at least 20 h.

Affinity separation matrix. In another embodiment the present invention is directed to an affinity separation matrix, comprising an Ig binding protein or Ig binding domain of the previous embodiments.

In preferred embodiments, the affinity separation matrix is a solid support. The affinity separation matrix comprises at least one Ig binding protein or Ig binding domain as described above.

An affinity matrix is useful for separation of immunoglobulins and should retain the Ig binding property even after highly alkaline conditions as applied during cleaning processes. Such cleaning of matrices is essential for long-term repeated use of matrices.

Solid support matrices for affinity chromatography are known in the art and include for example but are not limited to, agarose and stabilized derivatives of agarose (e.g. Praesto® Pure, Praesto® Jetted A50, Mabselect®, PrismA®, Sepharose 6B, CaptivA®, rPROTEIN A Sepharose Fast Flow, and other), cellulose or derivatives of cellulose, controlled pore glass (e.g. ProSep® vA resin), monolith (e.g. CIM® monoliths), silica, zirconium oxide (e.g. CM Zirconia or CPG®), titanium oxide, or synthetic polymers (e.g. polystyrene such as Poros 50A or Poros MabCapture® A resin, polyvinylether, polyvinyl alcohol, monodisperse polyacrylate resin (e.g. UniMab™, UniMab™Pro), polyhydroxyalkyl acrylates, polyhydroxyalkyl methacrylates, polyacrylamides, polymethacrylamides etc) and hydrogels of various compositions. In certain embodiments the support comprises a polyhydroxy polymer, such as a polysaccharide. Examples of polysaccharides suitable for supports include but are not limited to agar, agarose, dextran, starch, cellulose, pullulan, etc, and stabilized variants of these.

The formats for solid support matrices can be of any suitable well-known kind. Such solid support matrix for coupling the Ig binding protein or Ig binding domain as described herein might comprise for example, one of the following: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads or monodisperse polyacrylate beads. Suitable particle sizes may be in the diameter range of 5-500 μm, such as 10-100 μm, such as 20-80 μm, such as 40-70 μm. Matrices in particle form can be used as a packed bed or in a suspended form including expanded beds.

In an alternative embodiment, the solid support matrix is a membrane, for example a hydrogel membrane. In some embodiments, the affinity purification involves a membrane as matrix to which the Ig binding protein or Ig binding domain of the one embodiment is covalently bound. The solid support can also be in the form of a membrane in a cartridge.

In some embodiments, the affinity purification involves a chromatography column containing a solid support matrix to which the Ig binding protein or Ig binding domain of the one embodiment is covalently bound.

Immobilization to a solid support. In embodiments of the invention, the Ig binding protein or Ig binding domain is conjugated to a solid support. In some embodiments of the invention, the Ig binding protein or Ig binding domain may comprise additional amino acid residues at the N- and/or C-terminal end. The Ig binding protein or Ig binding domain of the invention may be attached to a suitable solid support matrix via conventional coupling techniques. Methods for immobilization of protein ligands to solid supports are well-known in this field and easily performed by the skilled person in this field using standard techniques and equipment. In some embodiments, the coupling may be a multipoint coupling, for example via several lysines, or a single point coupling, for example via cysteine.

In some embodiments, the alkaline stable Ig binding protein or Ig binding domain comprises an attachment site for covalent attachment to a solid phase (matrix). Site-specific attachment sites comprise natural amino acids, such as cysteine or lysine, which enable specific chemical reactions with a reactive group of the solid phase or a linker between the solid phase and the protein.

In some embodiments, the attachment site may be directly at the C- or N-terminal end of the Ig binding protein or Ig binding domain. In some embodiments, a single cysteine is located at the C-terminal end for site-specific immobilization of the Ig binding protein or Ig binding domain. An advantage of having a C-terminal cysteine is that coupling of the Ig binding protein or Ig binding domain can be achieved through reaction of the cysteine thiol with an electrophilic group on a support resulting in a thioether bridge coupling. This provides excellent mobility of the coupled protein which provides increased binding capacity.

In other embodiments, the attachment site may be located in the third helix of the Ig binding protein or Ig binding domain, for example, in position corresponding to position 43 or position 46 of SEQ. ID. NO: 1.

In other embodiments, there may be a linker between the N- or C-terminus and the attachment site. In some embodiments of the invention, the Ig binding protein or Ig binding domain may comprise a N- or C-terminal amino acid sequence of 3-20 amino acids, preferably of 4-10 amino acids, with a terminal cysteine. Amino acids for a terminal attachment site may be selected from the group of proline, glycine, alanine, and serine, with a single cysteine at the C-terminal end for coupling.

In some embodiments of the invention, the Ig binding protein or Ig binding domain may also comprise additional amino acid residues at the N- and/or C-terminal end, such as for example a leader sequence at the N-terminal end and/or a coupling sequence with or without a tag at the N- or C-terminal end.

Use of the Ig binding protein. In a one embodiment the present invention is directed to the use of the Ig binding protein or Ig binding domain of the one embodiment or an affinity matrix of the one embodiment for affinity purification of immunoglobulins or variants thereof, i.e. the Ig binding protein or Ig binding domain of the invention is used for affinity chromatography. In some embodiments, the Ig binding protein or Ig binding domain of the invention is immobilized onto a solid support as described in the one embodiment of the invention.

Method of affinity purification of immunoglobulins. In one embodiment the present invention is directed to a method of affinity purification of immunoglobulins, the method comprising the following steps:

(a) providing a liquid (sample) that contains an Ig such as $IgG_1$, $IgG_2$, $IgG_4$, IgM, IgA, Ig fragments, Fc fragments, or Fab fragments (including fusion proteins and conjugates, as defined above);

(b) providing an affinity separation matrix comprising an immobilized Ig binding protein or Ig binding domain as described above immobilized to said affinity separation matrix;

(c) contacting said liquid with said affinity separation matrix, under conditions that permit binding of the at least one Ig binding protein or Ig binding domain as described above to an Ig; and (d) eluting said Ig from said matrix, thereby obtaining an eluate containing said Ig.

In some embodiments, the method of affinity purification may further comprise one or more washing steps carried out between steps (c) and (d) under conditions sufficient to remove from the affinity separation matrix some or all molecules that are non-specifically bound thereto. Non-specifically bound means any binding that does not involve an interaction between the at least one Ig binding protein or Ig binding domain and an Ig.

Affinity separation matrices suitable for the disclosed uses and methods are those matrices according to the embodiments described above and as known to someone skilled in the art.

In some embodiments, the elution of the immunoglobulin from (the matrix comprising) the Ig binding protein or Ig binding domain in step (d) is effected through a change in pH and/or a change in salt concentration. In general, suitable conditions for performing the method of affinity purification are well known to someone skilled in the art. In some embodiments, the disclosed uses or methods of affinity purification comprising the disclosed Ig binding proteins or Ig binding domains may provide elution of at least about 95%, at least about 96%, at least about 97%, at least about 98%, at least about 99%, or 100% of Ig containing proteins at a pH of greater than or equal to 3.7 (e.g., about pH 4.0, about pH 4.5, about pH 5.0, or about pH 5.5). Due to the high stability of the Ig binding proteins and Ig binding domains of the invention, solutions with greater than or equal to pH 3.7 can be used for the elution of Ig proteins (see Examples).

In some embodiments, in step (d) of the method of affinity purification more than 95% of the protein comprising the Ig sequence (e.g. antibody) is eluted at pH 3.7 or higher (up to about pH 5.5) from the matrix comprising the immobilized Ig binding protein or Ig binding domain as described above. In some embodiments, a further step (e) for efficient cleaning of the affinity matrix is added, preferably by using an alkaline liquid, for example, with pH of 13-14. In certain embodiments, the cleaning liquid comprises 0.1-1.0 M NaOH or KOH, preferably 0.25-0.5 M NaOH or KOH. Due to the high alkaline stability of the Ig binding proteins or Ig binding domains of the invention, such strong alkaline solution can be used for cleaning purposes. After cleaning the affinity purification matrix with an alkaline cleaning liquid, in some embodiments, at least 88% of the Ig binding protein or Ig binding domain have Ig binding activity if incubated for at least 48 h at 0.5 M NaOH. In some embodiments, the Ig-binding capacity of the Ig binding protein or Ig binding domain is at least about 80%, at least about 90%, or 100% of the Ig binding capacity before the incubation under alkaline conditions, for example, as determined by the remaining Ig-binding capacity after at least 20 h incubation in 0.5 M NaOH.

The present invention further provides a method of isolating an immunoglobulin, comprising the steps (a) contacting a liquid sample comprising an immunoglobulin with a separation matrix comprising a plurality of Ig binding proteins or Ig binding domains (coupled to a solid support); (b) washing the separation matrix with a washing liquid at a pH above pH 3.7 (up to to 5.5); (c) eluting the immunoglobulin from the separation matrix; and (d) obtaining the immunoglobulin.

Nucleic acid molecule. In one embodiment, the present invention is directed to a nucleic acid molecule, preferably an isolated nucleic acid molecule, encoding an Ig binding protein or Ig binding domain as disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector.

In one embodiment, the present invention is directed to an expression system which comprises a nucleic acid or a vector as disclosed above, for example a prokaryotic host cell, for example *E. coli*, or a eukaryotic host, for example yeast *Saccharomyces cerevisiae* or *Pichia pastoris* or mammalian cells such as CHO cells.

Method for the production of a Ig binding protein. In one embodiment the present invention is directed to a method for the production of a Ig binding protein or Ig binding domain of the invention, comprising the step(s): (a) culturing the host cell of the one embodiment under suitable conditions for the expression of the binding protein or Ig binding domain in order to obtain said Ig binding protein or Ig binding domain; and (b) optionally isolating said Ig binding protein or Ig binding domain. Suitable conditions for culturing a prokaryotic or eukaryotic host are well-known to the person skilled in the art.

Ig binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

One embodiment of the present invention is directed to a method for the preparation of a Ig binding protein or Ig binding domain according to the invention as detailed above, said method comprising the following steps: (a) preparing a nucleic acid encoding an Ig binding protein or Ig binding domain as defined above; (b) introducing said nucleic acid into an expression vector; (c) introducing said expression vector into a host cell; (d) cultivating the host cell; (e) subjecting the host cell to culturing conditions under which an Ig binding protein or Ig binding domain is expressed, thereby (e) producing an Ig binding protein or Ig binding domain as described above; optionally (f) isolating the Ig binding protein or Ig binding domain produced in step (e); and (g) optionally conjugating the Ig binding protein or Ig binding domain to solid matrices as described above. In a further embodiment of the present invention the production of the Ig binding protein or Ig binding domain is performed by cell-free in vitro transcription/translation.

EXAMPLES

The following Examples are provided for further illustration of the invention. The invention, however, is not limited thereto, and the following Examples merely show the practicability of the invention on the basis of the above description.

Example 1. Generation of Ig Binding Proteins of the Invention

Modifications were introduced in SEQ ID NO: 1 (cs26) by site-saturation mutagenesis of individual amino acid residues. The following exchanges were introduced and analyzed for properties in affinity chromatography: 8I, 8F, 8Y, 8W, 8L, 8V, 6I, 6Y, 6W, 6L, 4I, 4F, 4W, 4Y, 4L; position 43 was exchanged to C (cysteine) for coupling to the matrix.

Example 2. Expression of Ig Binding Proteins

BL21 (DE3) competent cells were transformed with an expression plasmid encoding Ig binding proteins (for example, 203524 and 203550). Cells were spread onto selective agar plates (Kanamycin) and incubated either for 2 days at 21° C. or overnight at 37° C. Precultures were inoculated from single colony in 50 ml 2×YT medium supplemented with 50 µg/ml kanamycin and cultured for 17 hours at 37° C. at 210 rpm in a conventional orbital shaker in 250 mL Erlenmeyer flasks. The $OD_{600}$ readout should be in the range of 3.5-6. Main cultures were inoculated from previous overnight culture with an adjusted start-$OD_{600}$ of 0.3 in 300 ml superrich medium (modified H15 medium consisting of 2% glucose, 5% yeast extract, 0.89% glycerol, 0.76% lactose, 250 mM MOPS, 202 mM TRIS, 10 mM $MgSO_4$, pH 7.4, antifoam SE15) that was supplemented with 50 µg/ml Kanamycin and trace elements (see Studier 2005) in 1 L thick-walled Erlenmeyer flasks. Cultures were transferred to a resonant acoustic mixer ($RAM_{bio}$) and incubated at 37° C. with 20×g. Aeration was facilitated by Oxy-Pump stoppers. Recombinant protein expression was induced by metabolizing glucose and subsequently allowing lactose to enter the cells. Cells were grown overnight for approx. 18 hours to reach a final $OD_{600}$ of about 35-55. Before the harvest, the $OD_{600}$ was measured, samples adjusted to 0.6/$OD_{600}$ were withdrawn, pelleted and frozen at −20° C. To collect biomass cells were centrifuged at 12000×g for 20 min at 20° C. Pellets were weighed (wet weight). Cells were stored at −20° C. before processing.

Example 3: SDS-PAGE Analysis of Expression and Solubility of Ig Binding Proteins Samples were resuspended in 90 µl extraction buffer (PBS supplemented with 0.2 mg/ml Lysozyme, 0.5× BugBuster, 6 mM $MgSO_4$, 6 mM $MgCl_2$, 15 U/mL Benzonase) and solubilized by agitation in a thermomixer at 850 rpm, rt for 15 min with a subsequent incubation at −80° C. for 15 min. After thawing, soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 20 mM EDTA, pH 7.0). 35 µl were taken both from the soluble and insoluble fraction, and 10 µl 5× sample buffer as well as 5 µl 0.5 M DTT were added. Samples were boiled at 95° C. for 5 min. Finally, 5 µl of those samples were applied to NuPage Novex 4-12% Bis-Tris SDS gels which were run in accordance to the manufacturer's recommendations and stained with Coomassie. Results: High level expression was found under optimized conditions within the chosen period of time. All expressed Ig binding proteins were 100% soluble according to SDS-PAGE.

Example 4: Purification of Ig Binding Proteins

Ig binding proteins were expressed in the soluble fraction of *E. coli*. The cells were resuspended in cell disruption buffer and lysed by an ultrasonic cell disruption system (Sonopuls HD 2200, Bandelin). Purification step was performed with IEC Sepharose SP-HP (GE Healthcare) using an ÄKTAvant system (Ge Healthcare) according to the manufacturer's instructions using citric acid buffer at pH 3.0 (20 mM Citric acid, 1 mM EDTA, pH 3.0). Pure protein fractions were eluted by increasing sodium chloride concentration to 1 M with a linear gradient in 10 column volumes. Furth purification was performed by size exclusion chromatography (Superdex 75) according to manufactures instructions using citric acid buffer pH 6.0 (20 mM Citric acid, 150 mM NaCl, 1 mM EDTA, pH 6.0). Results: The purity of variants 8I and 6L was >95% after SE-HPLC and >90% after RP HPLC.

Example 5. The Ig Binding Proteins Bind to IgG with High Affinities (SPR)

A CM5 sensor chip (GE Healthcare) was equilibrated with surface plasmon resonance (SPR) running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization removes noncovalently bound Ig binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (µl/min). After each run, the chip surface was regenerated with regeneration buffer and equilibrated with running buffer. The control samples were applied to the matrix. Regeneration and re-equilibration were performed as previously mentioned. Binding studies were carried out by the use of the Biacore® 3000 (GE Healthcare) at 25° C.; data evaluation was operated via the BIAevaluation 3.0 software, provided by the manufacturer, by the use of the Langmuir 1:1 model (RI=0). Evaluated dissociation constants ($K_D$) were standardized against off-target and $K_D$ values of Ig binding proteins for Cetuximab ($IgG_1$), Natalizumab ($IgG_4$), and Panitumab ($IgG_2$) in Table 1.

TABLE 1

| | | $K_D$ values of Ig binding proteins for IgG | | |
|---|---|---|---|---|
| CID | Variant | vs. $hIgG_1$ (nM) | vs. $hIgG_2$ (nM) | vs. $hIgG_4$ (nM) |
| 203524 | D6L | 4.2 | 110 | 4 |
| 203550 | D8I | 2.9 | 20.6 | 2.4 |
| 203704 | N28H | 17.2 | 107 | 20 |
| 203447 | cs26 | 3.6 | 23.2 | 2.7 |

Example 6. Ig Binding Proteins Coupled to Agarose-Based Chromatography Beads Praesto™ Pure85—Coupling Efficiencies, DBC10%, Elution DBC10%: Purified Ig binding proteins were coupled to agarose-based chromatography beads (Praesto™ Pure85, Purolite; Cat. No. PR01265-164) according to the manufacturer's instructions (coupling conditions: pH 9.5, 3 hours, 35° C., 4.1 M $NaSO_4$, blocking overnight with ethanolamine). Coupled Resin was packed into super compact 5/50 column (Götec GmbH). Polyclonal human IgG Gammanorm® (Ocatpharm) was used as IgG sample (conc. 2.2 mg/ml). Polyclonal hIgG sample was applied in saturated amounts to the matrix comprising immobilized Ig binding protein. Results: Variant 8I (203550) shows slightly increased DBC10% in comparison to the parent variant (203447)

Elution of Immunoglobulin from matrix: The matrix was washed with 100 mM acetic acid buffer, pH 3.7 and then with 0.1 M phosphoric acid pH 1.7 to elute hIgG (Load: 2.2 mg/mL Gammanorm, 6 min residence time) that was bound to the immobilized Ig binding protein.

Results: For all variants tested, more than 99% of the antibody was eluted (e.g. D8I, D6L), compared to 96% elution if the parent molecule was immobilized; see Table 2.

Example 7. Alkaline Stability of Ig Binding Proteins Coupled to an Epoxy-Activated Matrix Columns were incubated with 0.5 M NaOH for 0 h and 20 h at room temperature (22° C.+/−3° C.). The Ig binding activity of the immobilized proteins was analyzed after incubation with 0.5 M NaOH. Results are shown in FIG. 2, FIG. 3, and FIG. 4. Praesto 85 epoxy resin with immobilized 25 mg/ml variants 6L (203524) and 8I (203550) and controls was incubated with 0.5 M NaOH for 50 h at room temperature (22° C.+/−3° C.). Results: Even after more than 2 days in strong alkaline solution, variant 8I and variant 6L showed 94.4% and 88.5%, respectively, remaining binding capacity for Ig. The remaining IgG binding capacity after alkaline treatment for 50 h is improved compared to the parent (caustic stable Ig binding protein of SEQ ID NO: 3; CID203447) (83% remaining binding capacity for Ig). Results see Table 2.

TABLE 2

| | | Caustic stability and elution | | | |
|---|---|---|---|---|---|
| CID | Affinity ligand | DBC10% at 6 min residence time (mg/ml) | DBC10 compared to cs26 | Caustic stability 50 h, 0.5M NaOH (%) | Elution recovery at 10 mM acetic acid at pH 3.7 |
| 203550 | cs26 8I | 56.6 | 103.1 | 94.4 | 99.6 |
| 203704 | cs26 28H | 56 | 102 | n.d. | n.d. |
| 203447 | cs26 | 54.9 | 100 | 83 | 99.8 |

Example 8. Elution of hIgG from Immobilized Ligands

Determination of elution pH with pH gradient. 1 mg/ml hIgG (Gammanorm) in PBS pH 7.3 was injected onto the column; contact time: 6 min. The column was washed with 0.1 M citrate pH 6.0. hIgG that was bound to the immobilized ligand was eluted via pH gradient form pH 6.0-2.0. The pH of the eluted main fraction was determined (peak maximum). Table 3 shows that all variants show a peak maximum at the range of pH 4.2 and pH 5.5, compared to cs26 a peak maximum of pH 3.7 for cs26.

TABLE 3

| | Elution pH (gradient) | | |
|---|---|---|---|
| SEQ ID NO: | CID | Substitution | Peak maximum (pH) |
| 3 | 203447 | | 3.7 |
| 60 | 203561 | Q10D | 4.6 |
| 59 | 203564 | Q10H | 5.3 |
| 58 | 203606 | Y14H | 5.5 |
| 57 | 203634 | I16H | 5.5 |
| 56 | 203648 | L17H | 4.9 |
| 55 | 203660 | H18E | 4.1 |
| 54 | 203702 | N28E | 4.3 |
| 53 | 203704 | N28H | 4.2 |

Elution at high pH (pH 4.5). The matrix was washed with 50 mM acetic acid buffer, pH 4.5 and then 100 mM acetic acid to elute hIgG (Load: 2.2 mg/mL Gammanorm, 6 min residence time) that was bound to the immobilized affinity ligand (variant). Table 4 shows that all ligands show significantly higher percentage of recovered antibody at pH 4.5 compared to cs26.

TABLE 4

| | | | Elution recovery (%) | |
|---|---|---|---|---|
| SEQ ID NO: | CID | ligand | 50 mM acetic acid pH 4.5 | 100 mM citrate pH 4.5 |
| 2 | 184244 | cs26 | 45 | n.d. |
| 60 | 203561 | cs26 10D | 85 | n.d. |
| 59 | 203564 | cs26 10H | 85 | n.d. |
| 58 | 203606 | cs26 14H | 98 | n.d. |
| 57 | 203634 | cs26 16H | 91 | n.d. |
| 56 | 203648 | cs26 17H | 82 | n.d. |
| 55 | 203660 | cs26 18E | 71 | n.d. |
| 54 | 203702 | cs26 28E | 70 | n.d. |
| 53 | 203704 | cs26 28H | 76 | 93.5 |

Example 9. Characterization of SEQ ID NO: 51 as Ligand for Affinity Purification of IgG Experiments were performed as described above, unless different procedures are mentioned here.

Purity: The purity of affinity ligand of SEQ ID NO: 51 was 100% after RP HPLC. Protein was detected by 220 nm absorption.

Affinity for $hIgG_1$: For the analysis of affinity ligand SEQ ID NO: 51, the monoclonal antibodies Cetuximab ($IgG_1$) and Belimumab ($IgG_1$) were used as target. The KD of SEQ ID NO: 51 for IgG Cetuximab was 40.8 nM and for $IgG_1$ Belimumab 47.4 nM.

Binding capacity: Binding capacity was determined with $IgG_1$ sample. The antibody was injected onto coupled resin with affinity ligand SEQ ID NO: 51 until 10% target breakthrough at 6 min residence time. Loaded antibody was quantified and calculated as dynamic binding capacity DBC10%, The DBC10% at 6 min residence time with 2.2 mg/ml Belimumab compared to cs26 was 104.1% compared to cs26.

Caustic stability: Praesto 85 epoxy resin with immobilized 19.6 mg/ml SEQ ID NO: 51 (coupled at pH=10.5 and 2.05 M $Na_2SO_4$) was incubated with 0.5 M NaOH for 24 h at room temperature (22° C.+/−3° C.). Even after 24 h in strong alkaline solution, SEQ ID NO: 51 showed no reduction in binding capacity for Ig (99%).

Elution pH: Elution pH of peak maximum was determined as described above. SEQ ID NO: 51 showed high elution pH (pH 5.0) for Gammanorm and Belimumab in comparison to cs26 (pH 3.5), see Table 5.

TABLE 5

| | Elution of peak maximum. | |
|---|---|---|
| Affinity ligand | Elution pH peak maximum; Target: Gammanorm | Elution pH peak maximum; Target: Belimumab |
| SEQ ID NO: 51 | 5.0 | 5.0 |
| cs26 | 3.5 | 3.5 |

Step Elution: Step elution was analyzed for target elution at pH 4.8. Residual elution of the target (Gammanorm or Belimumab) from the ligand (SEQ ID NO: 51) was analyzed after 100 mM phosphoric acid CIP at pH 1.7 (recovery). The target protein was nearly completely eluted from the ligand of SEQ ID NO: 51 at pH 4.8, see Table 6.

TABLE 6

| | Target elution at pH 4.8 compared to pH 1.7 | |
|---|---|---|
| Affinity ligand | Elution-Recovery at pH 4.8 vs. 1.7; Target: Gammanorm | Elution-Recovery at pH 4.8 vs. 1.7; Target: Belimumab |
| SEQ ID NO: 51 | 96.9% | 99.7% |
| cs26 | 15.8% | 19.3% |

The invention claimed is:

1. An Immunoglobulin (Ig) binding protein comprising one or more Ig binding domains,
   wherein at least one Ig binding domain comprises an amino acid sequence having at least 90% sequence identity to SEQ ID NO: 1, and isoleucine (I), leucine (L), valine (V), or an aromatic amino acid at the amino acid corresponding to position 8 of SEQ ID NO: 1, and
   wherein the Ig binding protein is stable under alkaline conditions of 0.5 M NaOH for at least 20 hours.

2. The Ig binding protein according to claim 1, wherein the amino acid corresponding to position 8 of SEQ ID NO: 1 is isoleucine (I) or tyrosine (Y).

3. The Ig binding protein according to claim 1, the at least one Ig binding domain further comprises histidine (H), aspartate (D), or glutamate (E) at one or more amino acids corresponding to position 10, 14, 16, 17, 18, or 28 of SEQ ID NO: 1.

4. The Ig binding protein according to claim 1, wherein the at least one Ig binding domain comprises an amino acid sequence having at least 95% sequence identity to any one of SEQ ID NOs: 4-9, 20-26, and 40-49, optionally having 100% sequence identity to any one of SEQ ID NOs: 4-9, 20-26, and 40-49.

5. The Ig binding protein according to claim 1, wherein said Ig binding protein binds to IgG$_1$, IgG$_2$, IgG$_4$, IgM, IgA, Ig fragments, Fc fragments, Fab fragments, fusion proteins comprising an Ig region, and conjugates comprising an Ig region.

6. The Ig binding protein according to claim 1, wherein the Ig binding protein comprises 2, 3, 4, 5, or 6 domains linked to each other.

7. The Ig binding protein according to claim 6, wherein the Ig binding protein is a homo-multimer or a hetero-multimer.

8. The Ig binding protein according to claim 1, wherein the Ig binding protein is immobilized on a solid support.

9. An affinity separation matrix comprising the Ig binding protein of claim 1 coupled to said affinity separation matrix.

10. A method for affinity purifying a protein comprising an Ig sequence, the method comprising:
    a. providing a liquid that contains a protein comprising an Ig sequence;
    b. providing an affinity separation matrix comprising at least one Ig binding protein of claim 1 coupled thereto;
    c. contacting said affinity separation matrix with the liquid under conditions that permit binding of the at least one Ig binding protein according to claim 1 to the protein comprising an Ig sequence; and
    d. eluting said protein comprising an Ig sequence from said affinity purification matrix,
    whereby the protein comprising an Ig sequence is affinity purified.

11. The method according to claim 10, wherein in step (d) the eluting is at pH 3.7 or higher and more than 95% of the protein comprising the Ig sequence is eluted from said affinity purification matrix.

12. The method according to claim 11, wherein in step (d) the eluting is at pH 4.5 or higher and more than 95% of the protein comprising the Ig sequence is eluted from said affinity purification matrix.

13. The method according to claim 11, further comprising (e) cleaning the affinity purification matrix with an alkaline cleaning liquid.

\* \* \* \* \*

```
                        SEQUENCE LISTING

<160> NUMBER OF SEQ ID NOS: 60

<210> SEQ ID NO 1
<211> LENGTH: 58
<212> TYPE: PRT
<213> ORGANISM: Artificial Sequence
<220> FEATURE:
<223> OTHER INFORMATION: Artificially synthesized cs26 (CID186352)

<400> SEQUENCE: 1

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Artificial Sequence
<220> FEATURE:
<223> OTHER INFORMATION: Artificially synthesized cs26 46C

<400> SEQUENCE: 2

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
```

-continued

```
                 35                  40                  45

Lys Lys Leu Asn Asp Ala Gln Ala Pro Lys
    50                  55

<210> SEQ ID NO 3
<211> LENGTH: 58
<212> TYPE: PRT
<213> ORGANISM: Artificial Sequence
<220> FEATURE:
<223> OTHER INFORMATION: Artificially synthesized cs26 43C (CID203447)

<400> SEQUENCE: 3

Ile Ala Ala Gln His Asp Lys Asp Gln Gln Ala Ala Phe Tyr Glu Ile
1               5                  10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 4
<211> LENGTH: 58
<212> TYPE: PRT
<213> ORGANISM: Artificial Sequence
<220> FEATURE:
<223> OTHER INFORMATION: Artificially synthesized cs26 D8I

<400> SEQUENCE: 4

Ile Ala Ala Gln His Asp Lys Ile Gln Gln Ala Ala Phe Tyr Glu Ile
1               5                  10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: Artificially synthesized cs26 8I 43C
      (CID203550)

<400> SEQUENCE: 5

Ile Ala Ala Gln His Asp Lys Ile Gln Gln Ala Ala Phe Tyr Glu Ile
1               5                  10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Artificially synthesized cs26 8F
```

-continued

```
<400> SEQUENCE: 6

Ile Ala Ala Gln His Asp Lys Phe Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: Artificially synthesized cs26 8Y (CID203532)

<400> SEQUENCE: 7

Ile Ala Ala Gln His Asp Lys Tyr Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Artificially synthesized cs26 8W

<400> SEQUENCE: 8

Ile Ala Ala Gln His Asp Lys Trp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Artificially synthesized cs26 8L

<400> SEQUENCE: 9

Ile Ala Ala Gln His Asp Lys Leu Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
```

-continued

```
    50                  55

<210> SEQ ID NO 10
<211> LENGTH: 58
<212> TYPE: PRT
<213> ORGANISM: Artificial Sequence
<220> FEATURE:
<223> OTHER INFORMATION: Artificially synthesized cs26 6I (CID203522)

<400> SEQUENCE: 10

Ile Ala Ala Gln His Ile Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Artificial Sequence
<220> FEATURE:
<223> OTHER INFORMATION: Artificially synthesized cs26 6Y (203531)

<400> SEQUENCE: 11

Ile Ala Ala Gln His Tyr Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 12
<211> LENGTH: 58
<212> TYPE: PRT
<213> ORGANISM: Artificial Sequence
<220> FEATURE:
<223> OTHER INFORMATION: Artificially synthesized cs26 6W

<400> SEQUENCE: 12

Ile Ala Ala Gln His Trp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 13
<211> LENGTH: 58
<212> TYPE: PRT
<213> ORGANISM: Artificial Sequence
<220> FEATURE:
<223> OTHER INFORMATION: Artificially synthesized cs26 6L

<400> SEQUENCE: 13

Ile Ala Ala Gln His Leu Lys Asp Gln Gln Ala Ala Phe Tyr Glu Ile
```

-continued

```
1               5                  10                 15

Leu His Leu Pro Asn Leu Thr Glu Glu Gln Arg Asn Ala Phe Ile Gln
            20                 25                 30

Ser Leu Arg Asp Asp Pro Ser Val Ser Leu Glu Ile Leu Ala Glu Ala
        35                 40                 45

Lys Lys Leu Asn Asp Ala Gln Ala Pro Lys
    50                 55

<210> SEQ ID NO 14
<211> LENGTH: 58
<212> TYPE: PRT
<213> ORGANISM: Artificial Sequence
<220> FEATURE:
<223> OTHER INFORMATION: Artificially synthesized cs26 6L 43C (203524)

<400> SEQUENCE: 14

Ile Ala Ala Gln His Leu Lys Asp Gln Gln Ala Ala Phe Tyr Glu Ile
1               5                  10                 15

Leu His Leu Pro Asn Leu Thr Glu Glu Gln Arg Asn Ala Phe Ile Gln
            20                 25                 30

Ser Leu Arg Asp Asp Pro Ser Val Ser Cys Glu Ile Leu Ala Glu Ala
        35                 40                 45

Lys Lys Leu Asn Asp Ala Gln Ala Pro Lys
    50                 55

<210> SEQ ID NO 15
<211> LENGTH: 58
<212> TYPE: PRT
<213> ORGANISM: Artificial Sequence
<220> FEATURE:
<223> OTHER INFORMATION: Artificially synthesized cs26 4I

<400> SEQUENCE: 15

Ile Ala Ala Ile His Asp Lys Asp Gln Gln Ala Ala Phe Tyr Glu Ile
1               5                  10                 15

Leu His Leu Pro Asn Leu Thr Glu Glu Gln Arg Asn Ala Phe Ile Gln
            20                 25                 30

Ser Leu Arg Asp Asp Pro Ser Val Ser Leu Glu Ile Leu Ala Glu Ala
        35                 40                 45

Lys Lys Leu Asn Asp Ala Gln Ala Pro Lys
    50                 55

<210> SEQ ID NO 16
<211> LENGTH: 58
<212> TYPE: PRT
<213> ORGANISM: Artificial Sequence
<220> FEATURE:
<223> OTHER INFORMATION: Artificially synthesized cs26 4F (203494)

<400> SEQUENCE: 16

Ile Ala Ala Phe His Asp Lys Asp Gln Gln Ala Ala Phe Tyr Glu Ile
1               5                  10                 15

Leu His Leu Pro Asn Leu Thr Glu Glu Gln Arg Asn Ala Phe Ile Gln
            20                 25                 30

Ser Leu Arg Asp Asp Pro Ser Val Ser Leu Glu Ile Leu Ala Glu Ala
        35                 40                 45

Lys Lys Leu Asn Asp Ala Gln Ala Pro Lys
    50                 55

<210> SEQ ID NO 17
```

-continued

```
<211> LENGTH: 58
<212> TYPE: PRT
<213> ORGANISM: Artificial Sequence
<220> FEATURE:
<223> OTHER INFORMATION: Artificially synthesized cs26 4W (203502)

<400> SEQUENCE: 17

Ile Ala Ala Trp His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Artificial Sequence
<220> FEATURE:
<223> OTHER INFORMATION: Artificially synthesized cs26 4L

<400> SEQUENCE: 18

Ile Ala Ala Leu His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Artificially synthesized cs26 4Y

<400> SEQUENCE: 19

Ile Ala Ala Tyr His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 20
<211> LENGTH: 58
<212> TYPE: PRT
<213> ORGANISM: Artificial Sequence
<220> FEATURE:
<223> OTHER INFORMATION: Artificially synthesized cs26 8I 14H

<400> SEQUENCE: 20

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Ala Phe Ile Gln
            20                  25                  30
```

```
Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Artificially synthesized cs26 8I 14H 46C

<400> SEQUENCE: 21

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Artificially synthesized cs26 8I 28H 46C

<400> SEQUENCE: 22

Ile Ala Ala Gln His Asp Lys Ile Gln Gln Ala Ala Phe Tyr Glu Ile
1               5                   10                  15

Leu His Leu Pro Asn Leu Thr Glu Glu Gln Arg His Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 23
<211> LENGTH: 56
<212> TYPE: PRT
<213> ORGANISM: Artificial Sequence
<220> FEATURE:
<223> OTHER INFORMATION: Artificially synthesized cs26 8I 14H 43C del1
      del2

<400> SEQUENCE: 23

Ala Gln His Asp Lys Ile Gln Gln Ala Ala Phe His Glu Ile Leu His
1               5                   10                  15

Leu Pro Asn Leu Thr Glu Glu Gln Arg Asn Ala Phe Ile Gln Ser Leu
            20                  25                  30

Arg Asp Asp Pro Ser Val Ser Leu Cys Ile Leu Ala Glu Ala Lys Lys
        35                  40                  45

Leu Asn Asp Ala Gln Ala Pro Lys
    50                  55

<210> SEQ ID NO 24
<211> LENGTH: 56
<212> TYPE: PRT
<213> ORGANISM: Artificial Sequence
```

<220> FEATURE:
<223> OTHER INFORMATION: Artificially synthesized cs26 8I 28H 43C del1
     del2

<400> SEQUENCE: 24

Ala Gln His Asp Lys Ile Gln Gln Ala Ala Phe Tyr Glu Ile Leu His
1               5                   10                  15

Leu Pro Asn Leu Thr Glu Glu Gln Arg His Ala Phe Ile Gln Ser Leu
            20                  25                  30

Arg Asp Asp Pro Ser Val Ser Leu Cys Ile Leu Ala Glu Ala Lys Lys
        35                  40                  45

Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Artificially synthesized cs27 8I

<400> SEQUENCE: 25

Ile Ala Ala Lys Phe Asp Glu Ile Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 26
<211> LENGTH: 58
<212> TYPE: PRT
<213> ORGANISM: Artificial Sequence
<220> FEATURE:
<223> OTHER INFORMATION: Artificially synthesized cs27 8I 14H

<400> SEQUENCE: 26

Ile Ala Ala Lys Phe Asp Glu Ile Gln Gln Ala Ala Phe His Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 27
<211> LENGTH: 58
<212> TYPE: PRT
<213> ORGANISM: Artificial Sequence
<220> FEATURE:
<223> OTHER INFORMATION: Artificially synthesized cs27 8I 28H

<400> SEQUENCE: 27

Ile Ala Ala Lys Phe Asp Glu Ile Gln Gln Ala Ala Phe Tyr Glu Ile
1               5                   10                  15

Leu His Leu Pro Asn Leu Thr Glu Glu Gln Arg His Ala Phe Ile Gln
            20                  25                  30

Ser Leu Arg Asp Asp Pro Ser Val Ser Leu Glu Val Leu Gly Glu Ala

```
            35                  40                  45

Gln Lys Leu Asn Asp Ser Gln Ala Pro Lys
    50                  55

<210> SEQ ID NO 28
<211> LENGTH: 58
<212> TYPE: PRT
<213> ORGANISM: Artificial Sequence
<220> FEATURE:
<223> OTHER INFORMATION: Artificially synthesized cs59 8I

<400> SEQUENCE: 28

Ile Asp Ala Lys Phe Asp Glu Ile Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 29
<211> LENGTH: 58
<212> TYPE: PRT
<213> ORGANISM: Artificial Sequence
<220> FEATURE:
<223> OTHER INFORMATION: Artificially synthesized cs59 8I 14H

<400> SEQUENCE: 29

Ile Asp Ala Lys Phe Asp Glu Ile Gln Gln Ala Ala Phe His Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 30
<211> LENGTH: 58
<212> TYPE: PRT
<213> ORGANISM: Artificial Sequence
<220> FEATURE:
<223> OTHER INFORMATION: Artificially synthesized cs59 8I 28H

<400> SEQUENCE: 30

Ile Asp Ala Lys Phe Asp Glu Ile Gln Gln Ala Ala Phe Tyr Glu Ile
1               5                   10                  15

Leu His Leu Pro Asn Leu Thr Glu Asp Gln Arg His Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 31
<211> LENGTH: 58
<212> TYPE: PRT
<213> ORGANISM: Artificial Sequence
<220> FEATURE:
<223> OTHER INFORMATION: Artificially synthesized cs60 8I
```

```
<400> SEQUENCE: 31

Ile Asp Ala Lys Phe Asp Glu Ile Ala Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 32
<211> LENGTH: 58
<212> TYPE: PRT
<213> ORGANISM: Artificial Sequence
<220> FEATURE:
<223> OTHER INFORMATION: Artificially synthesized cs60 8I 14H

<400> SEQUENCE: 32

Ile Asp Ala Lys Phe Asp Glu Ile Ala Gln Ala Ala Phe His Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 33
<211> LENGTH: 58
<212> TYPE: PRT
<213> ORGANISM: Artificial Sequence
<220> FEATURE:
<223> OTHER INFORMATION: Artificially synthesized cs60 8I 28H

<400> SEQUENCE: 33

Ile Asp Ala Lys Phe Asp Glu Ile Ala Gln Ala Ala Phe Tyr Glu Ile
1               5                   10                  15

Leu His Leu Pro Asn Leu Thr Glu Asp Gln Arg His Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro
    50                  55

<210> SEQ ID NO 34
<211> LENGTH: 58
<212> TYPE: PRT
<213> ORGANISM: Artificial Sequence
<220> FEATURE:
<223> OTHER INFORMATION: Artificially synthesized cs14 8I

<400> SEQUENCE: 34

Ile Ala Ala Lys His Asp Lys Ile Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55
```

-continued

<210> SEQ ID NO 35
<211> LENGTH: 58
<212> TYPE: PRT
<213> ORGANISM: Artificial Sequence
<220> FEATURE:
<223> OTHER INFORMATION: Artificially synthesized cs14 8I 14H

<400> SEQUENCE: 35

Ile Ala Ala Lys His Asp Lys Ile Gln Gln Ala Ala Phe His Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 36
<211> LENGTH: 58
<212> TYPE: PRT
<213> ORGANISM: Artificial Sequence
<220> FEATURE:
<223> OTHER INFORMATION: Artificially synthesized cs14 8I 28H

<400> SEQUENCE: 36

Ile Ala Ala Lys His Asp Lys Ile Gln Gln Ala Ala Phe Tyr Glu Ile
1               5                   10                  15

Leu His Leu Pro Asn Leu Thr Glu Asp Gln Arg His Ala Phe Ile Gln
            20                  25                  30

Ser Leu Arg Asp Asp Pro Ser Val Ser Leu Glu Ile Leu Gly Glu Ala
        35                  40                  45

Lys Lys Leu Asn Asp Ala Gln Ala Pro Pro
    50                  55

<210> SEQ ID NO 37
<211> LENGTH: 114
<212> TYPE: PRT
<213> ORGANISM: Artificial Sequence
<220> FEATURE:
<223> OTHER INFORMATION: Artificially synthesized dimer

<400> SEQUENCE: 37

Ala Gln His Asp Lys Ile Gln Gln Ala Ala Phe Tyr Glu Ile Leu His
1               5                   10                  15

Leu Pro Asn Leu Thr Glu Glu Gln Arg Asn Ala Phe Ile Gln Ser Leu
            20                  25                  30

Arg Asp Asp Pro Ser Val Ser Leu Cys Ile Leu Ala Glu Ala Lys Lys
        35                  40                  45

Leu Asn Asp Ala Gln Ala Pro Lys Ile Ala Ala Gln His Asp Lys Ile
    50                  55                  60

Gln Gln Ala Ala Phe Tyr Glu Ile Leu His Leu Pro Asn Leu Thr Glu
65                  70                  75                  80

Glu Gln Arg Asn Ala Phe Ile Gln Ser Leu Arg Asp Asp Pro Ser Val
                85                  90                  95

Ser Leu Glu Ile Leu Ala Glu Ala Lys Lys Leu Asn Asp Ala Gln Ala
            100                 105                 110

Pro Lys

```
<210> SEQ ID NO 38
<211> LENGTH: 58
<212> TYPE: PRT
<213> ORGANISM: Artificial Sequence
<220> FEATURE:
<223> OTHER INFORMATION: Artificially synthesized PAdelFc

<400> SEQUENCE: 38

Ile Ala Ala Gln His Asp Lys Asp Gln Ser Ala Ala Asp Ser Glu Ile
1               5                   10                  15

Leu His Leu Pro Asn Leu Thr Glu Glu Gln Arg Asn Ala Phe Arg Gln
            20                  25                  30

Ser Leu Ser Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 39
<211> LENGTH: 58
<212> TYPE: PRT
<213> ORGANISM: Artificial Sequence
<220> FEATURE:
<223> OTHER INFORMATION: Artificially synthesized PAdelFc

<400> SEQUENCE: 39

Ile Ala Ala Gln His Asp Lys Ile Gln Gln Ala Ala Asp Lys Glu Ile
1               5                   10                  15

Leu His Leu Pro Asn Leu Thr Glu Glu Gln Arg Asn Lys Phe Arg Gln
            20                  25                  30

Ser Leu Arg Asp Asp Pro Ser Val Ser Ala Glu Ile Leu Ala Glu Ala
        35                  40                  45

Lys Lys Leu Asn Asp Ala Gln Ala Pro Lys
    50                  55

<210> SEQ ID NO 40
<211> LENGTH: 56
<212> TYPE: PRT
<213> ORGANISM: Artificial Sequence
<220> FEATURE:
<223> OTHER INFORMATION: Artificially synthesized cs26 8I 14H 46C del2N

<400> SEQUENCE: 40

Ala Gln His Asp Lys Ile Gln Gln Ala Ala Phe His Glu Ile Leu His
1               5                   10                  15

Leu Pro Asn Leu Thr Glu Glu Gln Arg Asn Ala Phe Ile Gln Ser Leu
            20                  25                  30

Arg Asp Asp Pro Ser Val Ser Leu Glu Ile Leu Cys Glu Ala Lys Lys
        35                  40                  45

Leu Asn Asp Ala Gln Ala Pro Lys
    50                  55

<210> SEQ ID NO 41
<211> LENGTH: 59
<212> TYPE: PRT
<213> ORGANISM: Artificial Sequence
<220> FEATURE:
<223> OTHER INFORMATION: Artificially synthesized cs26 8I 14H 29K c-term
      cys

<400> SEQUENCE: 41

Ile Ala Ala Gln His Asp Lys Ile Gln Gln Ala Ala Phe His Glu Ile
1               5                   10                  15
```

-continued

```
Leu His Leu Pro Asn Leu Thr Glu Glu Gln Arg Asn Lys Phe Ile Gln
            20                  25                  30

Ser Leu Arg Asp Asp Pro Ser Val Ser Leu Glu Ile Leu Glu Glu Ala
        35                  40                  45

Lys Lys Leu Asn Asp Ala Gln Ala Pro Lys Cys
    50                  55

<210> SEQ ID NO 42
<211> LENGTH: 56
<212> TYPE: PRT
<213> ORGANISM: Artificial Sequence
<220> FEATURE:
<223> OTHER INFORMATION: Artificially synthesized cs26 8I 14H 29K del2N

<400> SEQUENCE: 42

Ala Gln His Asp Lys Ile Gln Gln Ala Ala Phe His Glu Ile Leu His
1               5                   10                  15

Leu Pro Asn Leu Thr Glu Glu Gln Arg Asn Lys Phe Ile Gln Ser Leu
            20                  25                  30

Arg Asp Asp Pro Ser Val Ser Leu Glu Ile Leu Ala Glu Ala Lys Lys
        35                  40                  45

Leu Asn Asp Ala Gln Ala Pro Lys
    50                  55

<210> SEQ ID NO 43
<211> LENGTH: 58
<212> TYPE: PRT
<213> ORGANISM: Artificial Sequence
<220> FEATURE:
<223> OTHER INFORMATION: Artificially synthesized cs26 8I 14H 29K

<400> SEQUENCE: 43

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Lys Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 44
<211> LENGTH: 47
<212> TYPE: PRT
<213> ORGANISM: Artificial Sequence
<220> FEATURE:
<223> OTHER INFORMATION: Artificially synthesized core of SEQ ID NO: 43

<400> SEQUENCE: 44

Ile Gln Gln Ala Ala Phe His Glu Ile Leu His Leu Pro Asn Leu Thr
1               5                   10                  15

Glu Glu Gln Arg Asn Lys Phe Ile Gln Ser Leu Arg Asp Asp Pro Ser
            20                  25                  30

Val Ser Leu Glu Ile Leu Ala Glu Ala Lys Lys Leu Asn Asp Ala
        35                  40                  45

<210> SEQ ID NO 45
<211> LENGTH: 58
<212> TYPE: PRT
<213> ORGANISM: Artificial Sequence
<220> FEATURE:
<223> OTHER INFORMATION: Artificially synthesized cs26 8I 14H 29K 43C
```

-continued

```
<400> SEQUENCE: 45

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Lys Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 46
<211> LENGTH: 56
<212> TYPE: PRT
<213> ORGANISM: Artificial Sequence
<220> FEATURE:
<223> OTHER INFORMATION: Artificially synthesized cs26 8I 14H 29K 46C
      del2N

<400> SEQUENCE: 46

Ala Gln His Asp Lys Ile Gln Gln Ala Ala Phe His Glu Ile Leu His
1               5                   10                  15

Leu Pro Asn Leu Thr Glu Glu Gln Arg Asn Lys Phe Ile Gln Ser Leu
            20                  25                  30

Arg Asp Asp Pro Ser Val Ser Leu Glu Ile Leu Cys Glu Ala Lys Lys
        35                  40                  45

Leu Asn Asp Ala Gln Ala Pro Lys
    50                  55

<210> SEQ ID NO 47
<211> LENGTH: 58
<212> TYPE: PRT
<213> ORGANISM: Artificial Sequence
<220> FEATURE:
<223> OTHER INFORMATION: Artificially synthesized cs26 8I 14H 29K 46C

<400> SEQUENCE: 47

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Lys Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 48
<211> LENGTH: 47
<212> TYPE: PRT
<213> ORGANISM: Artificial Sequence
<220> FEATURE:
<223> OTHER INFORMATION: Artificially synthesized core of SEQ ID NO: 47

<400> SEQUENCE: 48

Ile Gln Gln Ala Ala Phe His Glu Ile Leu His Leu Pro Asn Leu Thr
1               5                   10                  15

Glu Glu Gln Arg Asn Lys Phe Ile Gln Ser Leu Arg Asp Asp Pro Ser
            20                  25                  30

Val Ser Leu Glu Ile Leu Cys Glu Ala Lys Lys Leu Asn Asp Ala
        35                  40                  45
```

-continued

```
<210> SEQ ID NO 49
<211> LENGTH: 58
<212> TYPE: PRT
<213> ORGANISM: Artificial Sequence
<220> FEATURE:
<223> OTHER INFORMATION: Artificially synthesized cs26 8I 28H 29K 46C

<400> SEQUENCE: 49

Ile Ala Ala Gln His Asp Lys Ile Gln Gln Ala Ala Phe Tyr Glu Ile
1               5                   10                  15

Leu His Leu Pro Asn Leu Thr Glu Glu Gln Arg His Lys Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys
    50                  55

<210> SEQ ID NO 50
<211> LENGTH: 116
<212> TYPE: PRT
<213> ORGANISM: Artificial Sequence
<220> FEATURE:
<223> OTHER INFORMATION: Artificially synthesized dimer of SEQ ID NO: 21
      and SEQ ID NO: 20

<400> SEQUENCE: 50

Ile Ala Ala Gln His Asp Lys Ile Gln Gln Ala Ala Phe His Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Cys Glu Ala
        35                  40                  45

Lys Lys Leu Asn Asp Ala Gln Ala Pro Lys Ile Ala Ala Gln His Asp
    50                  55                  60

Lys Ile Gln Gln Ala Ala Phe His Glu Ile Leu His Leu Pro Asn Leu
65                  70                  75                  80

Thr Glu Glu Gln Arg Asn Ala Phe Ile Gln Ser Leu Arg Asp Asp Pro
                85                  90                  95

Ser Val Ser Leu Glu Ile Leu Ala Glu Ala Lys Lys Leu Asn Asp Ala
            100                 105                 110

Gln Ala Pro Lys
        115

<210> SEQ ID NO 51
<211> LENGTH: 114
<212> TYPE: PRT
<213> ORGANISM: Artificial Sequence
<220> FEATURE:
<223> OTHER INFORMATION: Artificially synthesized dimer of SEQ ID NO: 46
      and SEQ ID NO: 43

<400> SEQUENCE: 51

Ala Gln His Asp Lys Ile Gln Gln Ala Ala Phe His Glu Ile Leu His
1               5                   10                  15

Leu Pro Asn Leu Thr Glu Glu Gln Arg Asn Lys Phe Ile Gln Ser Leu
            20                  25                  30

Arg Asp Asp Pro Ser Val Ser Leu Glu Ile Leu Cys Glu Ala Lys Lys
        35                  40                  45

Leu Asn Asp Ala Gln Ala Pro Lys Ile Ala Ala Gln His Asp Lys Ile
    50                  55                  60
```

-continued

```
Gln Gln Ala Ala Phe His Glu Ile Leu His Leu Pro Asn Leu Thr Glu
65                  70                  75                  80

Glu Gln Arg Asn Lys Phe Ile Gln Ser Leu Arg Asp Asp Pro Ser Val
                85                  90                  95

Ser Leu Glu Ile Leu Ala Glu Ala Lys Lys Leu Asn Asp Ala Gln Ala
            100                 105                 110

Pro Lys

<210> SEQ ID NO 52
<211> LENGTH: 47
<212> TYPE: PRT
<213> ORGANISM: Artificial Sequence
<220> FEATURE:
<223> OTHER INFORMATION: Artificially synthesized consensus sequence of
      variants
<220> FEATURE:
<221> NAME/KEY: Xaa
<222> LOCATION: (1)..(1)
<223> OTHER INFORMATION: Xaa can be selected from Ile, Phe, Tyr, Trp,
      Leu, and Val
<220> FEATURE:
<221> NAME/KEY: Xaa
<222> LOCATION: (2)..(2)
<223> OTHER INFORMATION: Xaa can be selected from Gln and Ala
<220> FEATURE:
<221> NAME/KEY: Xaa
<222> LOCATION: (6)..(6)
<223> OTHER INFORMATION: Xaa can be selected from Asp and Phe
<220> FEATURE:
<221> NAME/KEY: Xaa
<222> LOCATION: (7)..(7)
<223> OTHER INFORMATION: Xaa can be selected from His and Tyr
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: Xaa
<222> LOCATION: (21)..(21)
<223> OTHER INFORMATION: Xaa can be selected from Asn and His
<220> FEATURE:
<221> NAME/KEY: Xaa
<222> LOCATION: (22)..(22)
<223> OTHER INFORMATION: Xaa can be selected from Ala and Lys
<220> FEATURE:
<221> NAME/KEY: Xaa
<222> LOCATION: (36)..(36)
<223> OTHER INFORMATION: Xaa can be selected from Glu and Cys
<220> FEATURE:
<221> NAME/KEY: Xaa
<222> LOCATION: (39)..(39)
<223> OTHER INFORMATION: Xaa can be selected from Ala, Gly, and Cys
<220> FEATURE:
<221> NAME/KEY: Xaa
<222> LOCATION: (42)..(42)
<223> OTHER INFORMATION: Xaa can be selected from Lys and Gln

<400> SEQUENCE: 52

Xaa Xaa Gln Ala Ala Phe Xaa Glu Ile Leu His Leu Pro Asn Leu Thr
1               5                   10                  15

Glu Xaa Gln Arg Xaa Xaa Phe Ile Gln Ser Leu Arg Asp Asp Pro Ser
            20                  25                  30

Val Ser Leu Xaa Ile Leu Xaa Glu Ala Xaa Lys Leu Asn Asp Ala
        35                  40                  45

<210> SEQ ID NO 53
<211> LENGTH: 58
<212> TYPE: PRT
<213> ORGANISM: Artificial Sequence
<220> FEATURE:
```

-continued

```
<223> OTHER INFORMATION: Artificially synthesized cs26 N28H (203704)

<400> SEQUENCE: 53

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg His Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 54
<211> LENGTH: 58
<212> TYPE: PRT
<213> ORGANISM: Artificial Sequence
<220> FEATURE:
<223> OTHER INFORMATION: Artificially synthesized cs26 N28E (203702)

<400> SEQUENCE: 54

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Glu Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 55
<211> LENGTH: 58
<212> TYPE: PRT
<213> ORGANISM: Artificial Sequence
<220> FEATURE:
<223> OTHER INFORMATION: Artificially synthesized cs26 18E (204660)

<400> SEQUENCE: 55

Ile Ala Ala Gln His Asp Lys Asp Gln Gln Ala Ala Phe Tyr Glu Ile
1               5                   10                  15

Leu Glu Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 56
<211> LENGTH: 58
<212> TYPE: PRT
<213> ORGANISM: Artificial Sequence
<220> FEATURE:
<223> OTHER INFORMATION: Artificially synthesized cs26 L17H (203648)

<400> SEQUENCE: 56

Ile Ala Ala Gln His Asp Lys Asp Gln Gln Ala Ala Phe Tyr Glu Ile
1               5                   10                  15

His His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45
```

-continued

```
Lys Lys Leu Asn Asp Ala Gln Ala Pro Lys
    50                  55

<210> SEQ ID NO 57
<211> LENGTH: 58
<212> TYPE: PRT
<213> ORGANISM: Artificial Sequence
<220> FEATURE:
<223> OTHER INFORMATION: Artificially synthesized cs26 I16H (203634)

<400> SEQUENCE: 57

Ile Ala Ala Gln His Asp Lys Asp Gln Gln Ala Ala Phe Tyr Glu His
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 58
<211> LENGTH: 58
<212> TYPE: PRT
<213> ORGANISM: Artificial Sequence
<220> FEATURE:
<223> OTHER INFORMATION: Artificially synthesized cs26 Y14H (203606)

<400> SEQUENCE: 58

Ile Ala Ala Gln His Asp Lys Asp Gln Gln Ala Ala Phe His Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 59
<211> LENGTH: 58
<212> TYPE: PRT
<213> ORGANISM: Artificial Sequence
<220> FEATURE:
<223> OTHER INFORMATION: Artificially synthesized cs26 Q10H (203564)

<400> SEQUENCE: 59

Ile Ala Ala Gln His Asp Lys Asp Gln His Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55

<210> SEQ ID NO 60
<211> LENGTH: 58
<212> TYPE: PRT
<213> ORGANISM: Artificial Sequence
<220> FEATURE:
<223> OTHER INFORMATION: Artificially synthesized cs26 Q10D (203561)

<400> SEQUENCE: 60
```

-continued

```
Ile Ala Ala Gln His Asp Lys Asp Gln Asp Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Cys Ile Leu Ala Glu Ala
        35                  40                  45

Lys Lys Leu Asn Asp Ala Gln Ala Pro Lys
    50                  55
```